(12) United States Patent
Niazi et al.

(10) Patent No.: US 11,311,603 B2
(45) Date of Patent: Apr. 26, 2022

(54) HIV TREATMENT COMPOSITIONS AND METHODS

(71) Applicant: NANTCELL, INC., Culver City, CA (US)

(72) Inventors: Kayvan Niazi, Culver City, CA (US); Jeffrey Safrit, Culver City, CA (US); John H. Lee, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

(21) Appl. No.: 16/443,560

(22) Filed: Jun. 17, 2019

(65) Prior Publication Data

US 2019/0381141 A1 Dec. 19, 2019

Related U.S. Application Data

(60) Provisional application No. 62/686,846, filed on Jun. 19, 2018.

(51) Int. Cl.

| | |
|---|---|
| *A61K 39/00* | (2006.01) |
| *C07K 16/30* | (2006.01) |
| *C07K 16/18* | (2006.01) |
| *A61K 39/395* | (2006.01) |
| *C07H 15/04* | (2006.01) |
| *A61K 38/20* | (2006.01) |
| *A61K 31/167* | (2006.01) |
| *A61K 31/4045* | (2006.01) |
| *A61K 31/192* | (2006.01) |
| *A61K 31/4406* | (2006.01) |
| *C07K 16/10* | (2006.01) |
| *A61K 31/215* | (2006.01) |
| *A61K 35/17* | (2015.01) |
| *C07K 14/735* | (2006.01) |
| *A61K 39/12* | (2006.01) |
| *A61K 31/506* | (2006.01) |

(52) U.S. Cl.
CPC ........ *A61K 38/2086* (2013.01); *A61K 31/167* (2013.01); *A61K 31/192* (2013.01); *A61K 31/215* (2013.01); *A61K 31/4045* (2013.01); *A61K 31/4406* (2013.01); *A61K 31/506* (2013.01); *A61K 35/17* (2013.01); *A61K 39/12* (2013.01); *C07K 14/70535* (2013.01); *C07K 16/1063* (2013.01)

(58) Field of Classification Search
CPC .............. A61P 35/00; A61K 2039/505; C07K 2317/24; C07K 2317/732; C07K 2317/92
See application file for complete search history.

(56) References Cited

U.S. PATENT DOCUMENTS 10,047,146 B2  8/2018  Mouquet et al.
2015/0183835 A1  7/2015  Carfi et al.

FOREIGN PATENT DOCUMENTS

| WO | 2008/097863 A3 | 11/2008 |
|---|---|---|
| WO | 2010067980 A2 | 6/2010 |
| WO | 2013/163427 A1 | 10/2013 |
| WO | 2013165592 A1 | 11/2013 |
| WO | 2016022358 A1 | 2/2016 |
| WO | 2016063251 A1 | 4/2016 |
| WO | 2016/154003 A1 | 9/2016 |
| WO | 2017/222619 A2 | 12/2017 |
| WO | 2018013975 A1 | 1/2018 |
| WO | WO2018013975 * | 1/2018 |
| WO | 2018075989 A1 | 4/2018 |
| WO | 2017/222619 A3 | 3/2019 |
| WO | 2019/245993 A1 | 12/2019 |

OTHER PUBLICATIONS

Sengupta, S. et al., Targeting the latent reservoir for HIV-1, Immunity, 2018, 48:872-895.*
Ferrari et al., "Humoral and Innate Antiviral Immunity as Tools to Clear Persistent HIV Infection", The Journal of Infectious Diseases, 2017, vol. 215, pp. S152-S159.
Bruel et al., "Elimination of HIV-1-infected cells by broadly neutralizing antibodies", Nature Communications, 2016, vol. 7, No. 10844, pp. 1-12.
Kramski et al., "HIV-specific Antibody Immunity Mediated Through NK Cells and Monocytes", Current HIV Research, 2013, vol. 11, pp. 388-406.
Amalfitano et al., "Production and Characterization of Improved Adenovirus Vectors with the E1, E2b, and E3 Genes Deleted", Journal of Virology, Feb. 1998, vol. 72, No. 2, pp. 926-933.
First Office Action received for Taiwanese Patent Application Serial No. 108121164 dated Mar. 24, 2020, 11 pages.
Jones, R. Brad et al., "A subset of latency-reversing agents 1,2,4,33-37 expose HIV-infected resting CD4+ T-cells to recognition by cytotoxic T-lymphocytes", PLOS Pathogens, 2016, vol. 12, No. 4, e1005545, pp. 1-25.
Sengupta, Srona et al., "Targeting the latent reservoir for HIV-1", 1-4,33-37, Immunity, May 15, 2018, vol. 48, pp. 872-895.
Garrido, Carolina et al., "Interleukin-15-stimulated natural killer cells clear HIV-1-infected cells following latency reversal Ex Vivo", Journal of Virology, May 29, 2018, vol. 92, issue 12, e00235-18, pp. 1-13.
International Search Report and Written Opinion received for PCT Application Serial No. PCTUS2019037537 dated Oct. 19, 2019, 12 pages.

(Continued)

*Primary Examiner* — Barry A Chestnut
(74) *Attorney, Agent, or Firm* — Martin Fessenmaier; Umberg Zipser LLP

(57) ABSTRACT

HIV treatment, and especially treatment of latent infected CD4 cells, can be significantly improved using a kick-and-kill approach that employs an immune stimulation component and/or HDAC inhibition as one treatment component, and that may also include a second component in which a vaccine composition, various NK cells, CAR-T cells, and/or broadly neutralizing antibodies are administered.

15 Claims, 16 Drawing Sheets

(56) References Cited

OTHER PUBLICATIONS

Office Action received for Taiwanese Patent Application Serial No. 108121164 dated Sep. 29, 2020, 16 pages (Including English Translation).
Davis et al., "A Phase 1 Study of ALT-803 (IL-15 Superagonist) to Clear Latent HIV Reservoirs", Poster # 356, p. 1.
Webb et al., "The human IL-15 superagonist ALT-803 directs SIV-specific CD8+ T cells into B-cell follicles", Blood Advances, vol. 2, No. 2, Jan. 23, 2018, pp. 9.
Iglesias-Ussel et al., "High Levels of CD2 Expression Identify HIV-1 Latently Infected Resting Memory CD4+ T Cells in Virally Suppressed Subjects", Journal of Virology, vol. 87, No. 6, Aug. 2013, pp. 9148-9158.
Communication pursuant to Rule 164(1) EPC received for European Patent Application Serial No. 19823605.1 dated Jul. 29, 2021, 18 pages.
First Examination Report received for CA Patent Application Serial No. 3100282 dated Feb. 16, 2022.
Communication pursuant to Rule 164(1) EPC received for European Application Serial No. 19823605.1 dated Jul. 29, 2021, 18 pages.
"A Phase 1 Study of ALT-803 (IL-15 Superagonist) to Clear Latent HIV Reservoirs", Conference on Retroviruses and Opportunistic Infections (CROI), URL: https://www.croiconference.org/abstract/phase-1-study-alt-803-il-15-superagonist-clear-latent-hiv-reservoirs/, 2018, 4 pages.
Seay et al., "In Vivo Activation of Human NK Cells by Treatment with an Interleukin-15 Superagonist Potently Inhibits Acute In Vivo HIV-1 Infection in Humanized Mice", Journal of Virology, 2015, vol. 89, No. 12, pp. 6264-6274.
Halper-Stromberg et al., "Broadly Neutralizing Antibodies and Viral inducers decrease rebound from HIV-1 latent reservoirs in humanized mice", Cell, vol. 158, No. 5, pp. 989-999.
Extended European Search Report received for European Patent Application Serial No. 19823605.1 dated Nov. 3, 2021, 15 pages.

* cited by examiner

HIV TREATMENT COMPOSITIONS AND METHODS

This application claims priority to our U.S. provisional patent application with the Ser. No. 62/686,846, which was filed Jun. 19, 2018.

FIELD OF THE INVENTION

The field of the invention is compositions and methods of latent viral infections, and especially as it relates to latent infection with HIV.

BACKGROUND

The following description includes information that may be useful in understanding the present invention. It is not an admission that any of the information provided herein is prior art or relevant to the presently claimed invention, or that any publication specifically or implicitly referenced is prior art.

While many antiretroviral drug treatments effectively suppress HIV replication, they are unfortunately not effective to cure infection. Underlying such lack of viral eradication is the establishment of latent infection in long-lived resting memory $CD4^+$ T-cells. Consequently, current antiviral therapy will result in a rapid viral rebound and disease progression when therapy is interrupted or terminated. More recently it was suggested that the viral reservoirs in resting memory $CD4^+$ T-cells can be attacked by combining latency reversal agents, which induce the expression of viral antigens, with selected immune effectors. This strategy is referred to as "kick and kill" or, alternatively, as "shock and kill". For example, targeting of reactivated infected cells with HIV-specific antibodies was reported, resulting in the engagement of natural killer (NK) cells, monocytes, and granulocytes which were thought to eliminate infected cells through antibody-dependent cell-mediated cytotoxicity (ADCC) and/or antibody-dependent cell-mediated phagocytosis (ADCP) (see e.g., *The Journal of infectious diseases* 215, S152-S159 (2017); *Nature communications* 7, 10844 (2016); and *Curr HIV Res* 11, 388-406 (2013)). While such strategies are at least conceptually attractive, they are not equally effective in clinical settings.

In other approaches, certain histone deacetylase (HDAC) inhibitors were employed to so reactivate latent HIV-1 proviruses from CD4+ T cell reservoir as described in WO2010/067980. Here, the inventors combined these HDAC inhibitors with a HAART cocktail to reduce the latent viral reservoir. In another approach, conventional antiretroviral therapy was combined with an HDAC inhibitor to trigger HIV reactivation. Unfortunately, however, combination of HDAC inhibitors with conventional antiretroviral agents was less than successful, possibly due to immune suppressive effects of the antiretroviral agents.

In further known approaches, an IL15 superagonist (ALT-803) was used to clear latent HIV reservoirs as described in "A Phase 1 Study Of Alt-803 (Il-15 Superagonist) To Clear Latent HIV Reservoirs" (Conference on retroviruses and Opportunistic Infections: Abstract 356, Mar. 4-7, 2018|Boston, Mass.). It was also observed that the IL-15 superagonist ALT-803 directed SIV-specific $CD8^+$ T cells into B-cell follicles. However, while generally well tolerated, ALT-803 was also less effective in generating persistent clearance of latent HIV reservoirs.

Thus, even though various methods of treating HIV are known in the art, all or almost all of them suffer from one or more disadvantages. Therefore, there is still a need for improved compositions and methods to improve treatment and/or clearance of latent HIV infected $CD4^+$ cells.

SUMMARY OF THE INVENTION

The inventive subject matter provides compositions and methods in which latent infected CD4 cells are subjected to a kick-and-kill approach that uses immune stimulation and/or HDAC inhibition as one treatment component that may be further augmented with a second component that includes vaccine compositions, various NK cells, CAR-T cells, and/or broadly neutralizing antibodies.

In one aspect of the inventive subject matter, the inventors contemplate a method of treating a latent HIV infected cell that includes a step of exposing the latent HIV infected cell to at least one of an immune stimulating cytokine or derivative thereof and a histone deacetylase (HDAC) inhibitor, wherein the immune stimulating cytokine or derivative thereof and/or the HDAC inhibitor are present at the infected cell at a concentration and for a time effective to trigger expression of viral antigens in the infected cell; and optionally another step of exposing the latent HIV infected cell to one or more of a (a) vaccine composition that generates an immune response against the viral antigen; (b) a natural killer cell that is optionally genetically modified to express a high affinity CD16 receptor or a chimeric antigen receptor; (c) a CAR-T cell; and/or (d) a broadly neutralizing antibody or antigen binding fragment thereof.

In some aspects, the immune stimulating cytokine or derivative thereof is ALT-803 or a T×M having a binding portion that binds to the viral antigen or an antigen on a CD4 T cell (e.g., CD2, CD20, or CD32), while in other aspects the HDAC inhibitor is vorinostat, panobinostat, valproic acid, phenylbutyrate, entinostat, CI-994, mocetinostat, Viracta 3996, dacinostat, pivanex, givinostat, or belinostat. Most typically, the step of exposing the latent HIV infected cell the immune stimulating cytokine or derivative thereof and/or the histone deacetylase (HDAC) inhibitor is performed in vivo. Furthermore, it is contemplated that the latent HIV infected cell is also exposed to one or more of the vaccine composition that generates an immune response against the viral antigen, the natural killer cell that is optionally genetically modified to express the high affinity CD16 receptor or the chimeric antigen receptor, the CAR-T cell, and the broadly neutralizing antibody.

With respect to the vaccine composition it is contemplated that the vaccine may be a bacterial vaccine, a yeast vaccine, and/or a viral vaccine, and that the vaccine composition comprises a recombinant nucleic acid that encodes at least one viral antigen. For example, where the vaccine is a bacterial vaccine it is preferred that the bacterial vaccine is an *E. coli* vaccine that is genetically engineered to have reduced or lack expression of a lipopolysaccharide. On the other hand, where the vaccine is a yeast vaccine, it is preferred that the yeast vaccine is an *S. cerevisiae* vaccine, and where the vaccine is a viral vaccine it is preferred that the viral vaccine is an adenoviral vaccine.

Moreover, with respect to the natural killer cell, it is contemplated that such cells typically include an autologous NK cell, an NK92 cell, an aNK cell, a haNK cell, or a taNK cell. Regarding suitable CAR-T cells it is contemplated that the CAR-T cells have a chimeric antigen receptor with an ectodomain that binds to CD2, CD20, or CD32. Regarding the broadly neutralizing antibody it is generally preferred that the antibody binds to gp120, and more typically to a gp41 interface site of gp120, a V1/V2-glycan site of gp120, a V3-glycan site of gp120, or a CD4 binding site of gp120.

Consequently, the inventors also contemplate a method of treating an individual that carries latent HIV infected cells. Such treatment methods will typically include a step of administering to the individual at least one of an immune stimulating cytokine or derivative thereof and a histone deacetylase (HDAC) inhibitor. Most typically, the immune stimulating cytokine or derivative thereof and/or the HDAC inhibitor are administered at a dosage and schedule effective to trigger expression of viral antigens in the infected cell. Where desired, such methods may also include a step of administering to the individual one or more of (a) a vaccine composition that generates an immune response against the viral antigen; (b) a natural killer cell that is optionally genetically modified to express a high affinity CD16 receptor or a chimeric antigen receptor; (c) a CAR-T cell; and (d) a broadly neutralizing antibody or antigen binding fragment thereof. Most typically, the step of administering to the individual at least one of the immune stimulating cytokine or derivative thereof and the histone deacetylase (HDAC) inhibitor and the step of administering the one or more of the vaccine composition that generates an immune response against the viral antigen, the natural killer cell that is optionally genetically modified to express the high affinity CD16 receptor or the chimeric antigen receptor, the CAR-T cell, and the broadly neutralizing antibody are performed sequentially with at least 24 hours between the steps.

In another aspect of the inventive subject matter, the inventors also contemplate a vaccine composition that comprises a recombinant nucleic acid that encodes at least one viral antigen of HIV, wherein the vaccine composition is formulated as a bacterial vaccine, as a yeast vaccine, or as a viral vaccine. Most typically, the bacterial vaccine is an *E. coli* vaccine that is genetically engineered to have reduced or lack expression of a lipopolysaccharide, the yeast vaccine is an *S. cerevisiae* vaccine, and the viral vaccine is an adenoviral vaccine. As will be appreciated, the viral antigen of HIV is gp120, gp160, gp41/gp160, or p24.

In yet another aspect of the inventive subject matter, the inventors contemplate a genetically engineered NK cell that includes a recombinant nucleic acid comprising a segment that encodes a chimeric antigen receptor with an ectodomain that binds to CD2, CD20, or CD32. Also contemplated are genetically engineered T cells that include a recombinant nucleic acid comprising a segment that encodes a chimeric antigen receptor with an ectodomain that binds to CD2, CD20, or CD32.

In a still further aspect of the inventive subject matter, the inventors contemplate a treatment kit that includes a haNK cell and a broadly neutralizing antibody against an HIV virus (with the antibody optionally bound to CD16 receptor of the haNK cell.

In addition, a TxM is contemplated having an ALT-803 portion and at least one affinity portion, wherein the affinity portion binds to a viral antigen or an antigen on a CD4 T cell.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 6A-6D are exemplary results for breadth and potency of neutralization of a panel of bNAbs against reactivated reservoir viruses: (6A) Representative neutralization curves against virus isolates #1 & #3 from study participant OM5162. Each graph represents antibodies targeting similar epitopes against one virus, and each curve represents results from one bNAb. (6B) The half maximal inhibitory concentration ($IC_{50}$) and (6C) $IC_{80}$ are shown in heat-maps. The lower the antibody concentration, the more sensitive the reservoir virus is to a specific bNAb (bNAbs were shown by binding epitope classes; HIV-IG, positive control antibody; 4G2-Hu, negative control antibody). The geometric mean concentration against all 36 (or 35) reservoir viruses tested was calculated. (6D) Heat-map showing neutralization coverage of antibody combinations. Shown are the % of viral isolates that were neutralized by at least one antibody in the indicated combinations using an $IC_{80}$ cut off of 10 µg/mL.

FIGS. 7A-7D show exemplary results for breadth and potency of binding of a panel of bNAbs against reactivated reservoir viruses. (7A) Representative flow plots showing bNAb binding to cells infected with reservoir viruses, gated on live/$CD3^+$ cell populations. For each bNAb/virus combination we calculated a median intensity fluorescence (MFI) ratio, defined as MFI of bnAbs in HIV infected cell population ($Gag^+$)/MFI of bnAbs in HIV uninfected cell population ($Gag^-$). The displayed plots provide an example intra-participant diversity in bNAb binding to different viral isolates. (7B) Heat-map showing binding of bNAbs at 5 µg/mL to the indicated viral isolates. The numbers given are MFI ratios, with higher values indicating higher levels of binding. (7C) Heat-map showing binding of each bNAb to infected cells when tested at its $IC_{80}$ neutralization concentration. (7D) Heat-map showing binding coverage (MFI ratio>2) of single bNAbs and all two bNAb concentrations. The breadth of coverage of antibody combinations was defined based on having at least one of the two bNAbs bind with an MFI ratio>2.

FIGS. 9A & 9B depict results for correlations between virus neutralization and paired late-infected cell binding at 5 µg/mL bNAb concentrations. Shown are correlations between $IC_{80}$ virus neutralization values and binding to late-infected cells (Gag⁺CD4⁻) using a 5 µg/mL concentration for each antibody. (9A) Correlation for all antibodies tested together. (9B) Correlations for each bNAb tested independently. Each virus/bNAb combination is indicated by a circle, and each color represents one study participant. Correlations were analyzed by Spearman correlation coefficient (r), with statistical significance highlighted in red letters.

DETAILED DESCRIPTION

The inventors have now discovered that HIV treatment, and especially treatment of latent infected CD4 cells, can be significantly improved using a kick-and-kill approach that employs an immune stimulation component and/or HDAC inhibition as one treatment component, and that preferably (but not necessarily) also includes a second component in which one or more of a vaccine composition, various NK cells, CAR-T cells, and broadly neutralizing antibodies are administered.

Figure 1:
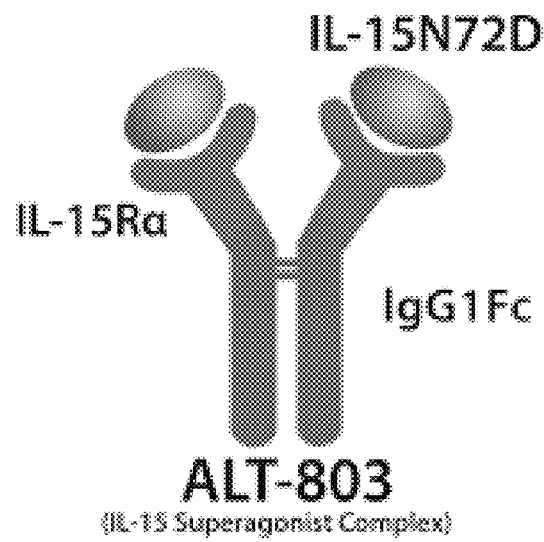
FIG. 1 is a schematic illustration of ALT-803.

Most notably, and among other findings, the inventors have now observed that IL-15, and especially enhanced forms of IL-15 alone or in combination with an HDAC inhibitor can elicit viral protein production in a latent infected cell. Moreover, as IL-15 also acts as an immune stimulatory cytokine, IL-15 and especially ALT-803 (Altor Bioscience, 3958, 2810 N Commerce Pkwy, Miramar, Fla. 33025) will produce an immune stimulatory effect upon reactivation of the latent virus and as such assist in immunological clearance of the virus and the infected cells, potentially due to activation of NK and CD8+ T cells. Therefore, it is generally preferred that at least the 'kick' phase in the 'kick-and-kill' approach may be achieved by administration of ALT-803, typically at dosages and a schedule as is known from cancer immune therapy using ALT-803. FIG. 1 exemplarily and schematically depicts ALT-803. Likewise, HDAC inhibitor dosages and schedules will parallel currently known dosages and schedules in cancer therapy.

Moreover, due to the pleiotropic effects of IL-15, and especially ALT-803 (and variants thereof), additional immune therapeutic agents will further (synergistically) enhance the antiviral effect. For example, where the immune therapeutic agent is a vaccine, the immune stimulating cytokine will significantly increase T cell and NK cells proliferation and activation, which will be targeted against the viral proteins and cells presenting such protein. Similarly, where the immune therapeutic agent is an NK and/or CAR-T cell, the immune stimulating cytokine will increase proliferation and cytotoxicity of the NK and/or CAR-T cells. Likewise, where the immune therapeutic agent is a broadly neutralizing antibody or antigen binding fragment thereof, the immune stimulating cytokine will increase ADCC via activated cytotoxic T cells or NK cells (particularly where the NK cell has a high-affinity CD16).

For example, and with respect to the immune stimulating cytokine or derivative thereof it is contemplated that suitable dosages for ALT-803 will be between 0.1-50 µg/kg, and more typically between 0.1-0.5 µg/kg, or between 0.5-5.0 µg/kg, or between 1-10 µg/kg. Thus, suitable dosages will be at least 0.5 µg/kg, or at least 1.0 µg/kg, or at least 2.0 µg/kg, or at least 5.0 µg/kg, or at least 7.0 µg/kg. Administration may be intravenous and/or subcutaneous. Similarly, suitable HDAC dosages (for example, for vorinostat) are typically between 50-10,000 mg per administration, or between 100-1,000 mg per administration, or between 400-2,500 mg per administration, or between 800-5,000 mg per administration, or between 2,000-10,000 mg per administration. Therefore, suitable dosages will be at least 400 mg, or at least 800 mg, or at least 1,200 mg, or at least 2,000 mg, or at least 4,000 mg. Administration is preferably oral. Further suitable HDAC inhibitors include panobinostat, valproic acid, phenylbutyrate, entinostat, CI-994, mocetinostat, Viracta VRx-3996 (2533 S Coast Hwy 101 Suite 210, Cardiff, Calif. 92007)), dacinostat, pivanex, givinostat, and belinostat, and suitable dosages are generally at, below, or above dosages that are published or otherwise recommended for such HDAC inhibitors.

Figure 2:
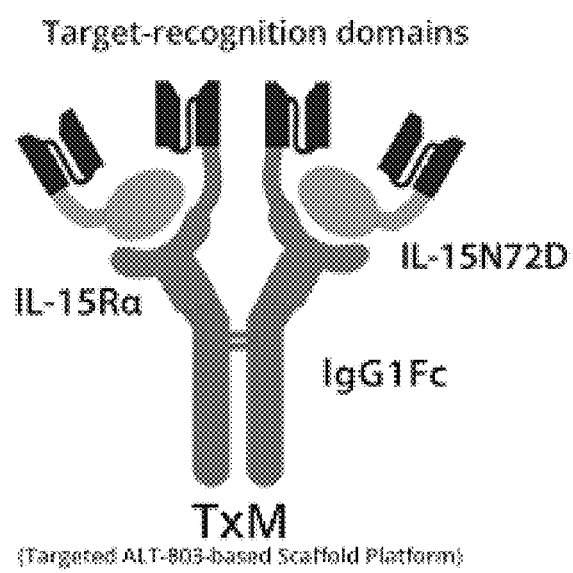
FIG. 2 is a schematic illustration of a TxM.

In still further aspects of the inventive subject matter, it is especially contemplated that the immune stimulation can be rendered more specific to the latent infected cells. To that end, a TxM can be constructed (see Altor Bioscience, 3958, 2810 N Commerce Pkwy, Miramar, Fla. 33025) that includes at least one affinity portion (e.g., scFv portion) that targets one or more antigens on latent infected cells. FIG. 2 exemplarily depicts a TxM having various binding (affinity) portions configured as scFv. For example, especially suitable antigens indicative of latent HIV infection include those in Table 1. However, particularly preferred targets that can be bound by the binding portion include CD2, CD4, CD20, and/or CD32.

TABLE 1

| Function | Gene |
|---|---|
| TCR associated | CD2 |
| | CD3δ |
| | CD4 |
| | CD6 |
| | CD38 |
| | CD278/ICOS |
| TNFR family | CD262 |
| | CD270 |
| | APO-3 |
| TNF family | CD40L |
| | CD70 |
| Cytokine receptors | CD124/IL4RA |
| | CD130/IL6RB |
| | CD218A/IL18RA |
| | CD218B/IL18RB |
| | IFNGR2 |
| Chemokine receptors | CD197/CCR7 |
| | CD184/CXCR4 |
| Other | CD32 |
| | CD69 |

Of course, it should be appreciated that such TxM molecules can include identical or different affinity portions. Regardless of the type of affinity portion, it should be noted that the TxM also provides immune stimulation as well as a triggering signal for expression of viral proteins in latent infected cells. Therefore, it should be noted that the 'kick-and-kill' strategy may be achieved by administration of an immune stimulating cytokine or enhanced immune stimulating cytokine (such as ALT-803 and/or TxM), alone or in combination with an HDAC inhibitor.

However, in further contemplated aspects of the inventive subject matter, the treatment may be further expanded to include administration of (a) a vaccine composition that generates an immune response against the viral antigen; (b) a natural killer cell that is optionally genetically modified to express a high affinity CD16 receptor or a chimeric antigen receptor; (c) a CAR-T cell; and/or (d) a broadly neutralizing antibody or antigen binding fragment thereof.

Vaccine formulations will typically include bacterial vaccine formulations, yeast vaccine formulations, and viral vaccine formulations, which will typically be recombinant vaccines that include a segment that encodes one or more HIV antigens. Moreover, it is noted that the vaccine formulations may also encode patient specific HIV antigens, that is, antigen fragments that are determined in silico to bind to an individual's MHC type. Moreover, it is generally preferred that the vaccines will target the latent (i.e., early) virus in infection. While numerous HIV antigens are deemed suitable for use in preparation of a vaccine, it is generally preferred that the antigen targeted is the gag (poly) protein of HIV.

With respect to bacterial vaccine formulations, it is generally contemplated that such vaccines include a genetically-engineered bacterium, which constitutively or inducibly expresses the HIV-related antigen. Regardless of the manner of expression, the genetically-engineered bacteria may be irradiated or otherwise rendered replication deficient or killed. The recombinant nucleotide sequence encoding a desired HIV-related antigen can then be inserted into a cassette and cloned into a vector with specific promoters so that it can be expressed in the bacterium. While any suitable vectors for expressing proteins can be used, it is preferred that vectors that can carry a cassette size of at least 1 k, preferably 2 k, more preferably 5 k base pairs. Most preferably, cassettes are contemplated that can be subcloned into different vectors to so facilitate generation of different recombinant entities (e.g., yeast and/or virus) carrying the same cassette.

One exemplary bacteria strain with modified lipopolysaccharides includes ClearColi® BL21(DE3) electrocompetent cells. This bacteria strain is BL21 with a genotype F-ompT hsdSB (rB– mB–) gal dcm lon λ(DE3 [lac' lacUV5-T7 gene 1 ind1 sam7 nin5]) msbA148 ΔgutQΔkdsD ΔlpxLΔlpxMΔpagPΔlpxPΔeptA. In this context, it should be appreciated that several specific deletion mutations (ΔgutQ/ ΔkdsD ΔlpxL ΔlpxMΔpagPΔlpxPΔeptA) encode the modification of LPS to Lipid $IV_A$, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4 (TLR4) in complex with myeloid differentiation factor 2 (MD-2), causing activation of NF-kB and production of proinflammatory cytokines. Lipid $IV_A$, which contains only four acyl chains, is not recognized by TLR4 and thus does not trigger an endotoxic response. While electrocompetent BL21 bacteria is provided as an example, the inventors contemplate that the genetically modified bacteria can be also chemically competent bacteria.

Alternatively, the inventors also contemplate that the patient's own endosymbiotic bacteria can be used as a vehicle to express the HIV-related antigen in vivo to elicit an immune response. As used herein, the patient's endosymbiotic bacteria refers bacteria residing in the patient's body regardless of the patient's health condition without invoking any substantial immune response. Thus, it is contemplated that the patient's endosymbiotic bacteria is a normal flora of the patient. For example, the patient's endosymbiotic bacteria may include *E. coli* or *Streptococcus* that can be commonly found in human intestine or stomach. In these embodiments, the patient's own endosymbiotic bacteria can be obtained from a biopsy sample or from a biological sample (e.g., saliva, stool, etc.). The patient's endosymbiotic bacteria can then be cultured in vitro and transfected with nucleotides encoding human disease-related antigen(s).

Therefore, it should be appreciated that the bacteria used in the methods presented herein may be from a strain that produces LPS, or that are genetically engineered to have reduced or abrogated expression of one or more enzymes leading to the formation of LPS that is recognized by a TLR, and particularly TLR4. Most typically, such bacteria will be genetically modified to express in an inducible manner at least one HIV-related antigen. Among other options, induction of expression may be done with synthetic compounds that are not ordinarily found in a mammal (e.g., IPTG, substituted benzenes, cyclohexanone-related compounds) or with compounds that naturally occur in a mammal (e.g., sugars (including 1-arabinose, 1-rhamnose, xylose, and sucrose), ε-caprolactam, propionate, or peptides), or induction may be under the control of one or more environmental factors (e.g., temperature or oxygen sensitive promoter). Most typically, the bacteria in the bacterial vaccine will be heat inactivated or irradiated to render the cells no longer capable of reproduction in a patient.

Similarly, with respect to yeast vaccine formulations, it is contemplated that numerous yeast organisms may be used in conjunction with the teachings presented herein. However, especially preferred yeast organisms include various species of the genera *Saccharomyces, Pichia, Cryptococcus, Candida, Hansenula,* Schizosachharomyces, and *Kluyveromyces*. As noted for the bacterial vaccine above, the yeast is preferably a recombinant yeast that is transfected to express at least at least one HIV-related antigen. For example, suitable yeast strains and methods of producing vaccines are described in WO 2008/097863. Moreover, it should be appreciated that the recombinant nucleic acid in the yeast or bacterial vaccine may encode a single antigen or multiple antigens (typically configured as a polytope).

With respect to viral vaccine formulations, it should be noted that the virus is genetically modified with a nucleic acid construct that leads to expression of at least one of the antigenic proteins or peptides. For example, suitable viruses include adenoviruses, adeno-associated viruses, alphaviruses, herpes viruses, lentiviruses, etc. However, adenoviruses are particularly preferred. Moreover, it is further preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933).

Regardless of the type of recombinant virus it is contemplated that the virus may be used to infect patient (or non-patient) cells ex vivo or in vivo. For example, the virus may be injected subcutaneously or intravenously, or may be administered intranasaly or via inhalation to so infect the patients cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. In other embodiments, the immune therapy need not rely on a virus but may also be effected with nucleic acid transfection or vaccination using RNA or DNA, or other recombinant vectors that lead to the expression of the desired antigen or antigens (e.g., as single peptides, tandem mini-gene, etc.) in desired cells, and especially immune competent cells.

Most typically, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc. Suitable exemplary viral expression constructs for use herein are described in WO 2017/222619. Moreover, it is contemplated that the antigens encoded in the recombinant nucleic acid may be selected for binding to a patient's MHC type, for example, using NetMHC2.0 or other known software.

In addition (or as alternative) to contemplated vaccine treatments, suitable treatments and methods may also include transfusion of autologous or heterologous NK cells to a patient, and particularly NK cells that are genetically modified to exhibit less cytotoxic cell killing inhibition. For example, the genetically modified NK cell may be a NK-92 derivative that is modified to have a reduced or abolished expression of at least one killer cell immunoglobulin-like receptor (KIR), which will render such cells constitutively activated. Of course, it should be noted that one or more KIRs may be deleted or that their expression may be suppressed (e.g., via miRNA, siRNA, etc.), including KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may be commercially obtained from NantKwest as aNK cells ('activated natural killer cells). In addition, contemplated NK cells suitable for use herein also include those that have abolished or silenced expression of NKG2A, which is an activating signal to Tregs and MDSCs. As will be readily appreciated, the immune stimulatory cytokine, ALT-803, or TxM as described above will activate NK cells and as such amplify the biological activity of the NK cells described herein.

Alternatively, the genetically engineered NK cell may also be an NK-92 derivative that is modified to express a high-affinity Fcγ receptor (CD16-158V). Sequences for high-affinity variants of the Fcγ receptor are well known in the art, and all manners of generating and expression are deemed suitable for use herein. Expression of such receptor is believed to allow specific targeting of latent infected cells using broadly neutralizing antibodies as are well known in the art. Advantageously, such cells may be commercially obtained from NantKwest as haNK cells ('high-affinity natural killer cells) and may then be further modified (e.g., to express co-stimulatory molecules). For example, haNK cells may be co-administered with antibodies targeting CD20. Moreover, it should be appreciated that haNK cells may be 'preloaded' with one or more targeting antibodies, such as broadly neutralizing antibodies and/or antibodies that specifically or preferentially bind to latent infected cells (for suitable markers see Table 1). Alternatively, the haNK cells may also be sequentially administered with suitable antibodies, with the antibodies typically being administered before cell transfusion.

In further aspects, genetically engineered NK cells and/or T cells may also be genetically engineered to express a chimeric T cell receptor. In especially preferred aspects, the chimeric T cell receptor will have a scFv portion or other ectodomain with binding specificity against the latent HIV infected cells, and suitable targets for T cell binding include the markers of Table 1 above. Alternatively, thusly genetically engineered NK cells may be commercially obtained from NantKwest as taNK cells ('target-activated natural killer cells') and further modified as desired. For example, suitable taNK cells may express a chimeric antigen receptor targeting CD20, CD32, or CD4. As will be readily appreciated, the ectodomain of the chimeric antigen receptor in the CAR-T cells or taNK cells may also be derived from anergic cells of the patient.

Additionally, or alternatively, it is also contemplated that broadly neutralizing antibodies or antigen binding fragments thereof may be employed as a portion of the kill phase in treatment options contemplated herein. Of course, it should be appreciated that these antibodies may act in concert with NK cells, and especially haNK cells, and/or may be independently administered to the patient. Moreover, it should be noted that the NK cells may be autologous (due to increased proliferation after ALT-803 administration), or allogenic NK cells (e.g., haNK cells CARt-haNK cells, etc.). With respect to the neutralizing antibodies it is contemplated that all known broadly neutralizing antibodies are deemed suitable for use herein, and appropriate broadly neutralizing antibodies include those targeting V3 glycan, CD4bs, gp41MPER, V1/V2, N332 glycan supersite, etc. Therefore, suitable broadly neutralizing antibodies include 10-1074, 2F512A12, 3BNC176, 3BNC117, 3BNC62, 4E1, CAP256-VRC26.01, HGN194, PGT151, PGT152, Z13, etc. Further suitable broadly neutralizing antibodies can be found at URL:bnaber.org. Of course, it should be appreciated that more than a single type of antibody may be employed. Moreover, broadly neutralizing antibodies need not be limited to IgG molecules, but also include antigen binding fragments such as Fabs and scFvs.

Therefore, it should be appreciated that the kick-and-kill strategy to trigger activation of latent viruses and elimination of viral reservoirs can be achieved in various manners that will combine triggering of viral protein expression in infected cells with immune stimulation and/or immune support. For example, and as already pointed out above, the kick-phase could be achieved by administration of ALT-803 or CD4 (or CD2, CD20, CD32)-targeted TxM, and/or administration of an HDAC inhibitor (e.g., Viracta VRx-3996 (2533 S Coast Hwy 101 Suite 210, Cardiff, Calif. 92007)), while the kill-phase will preferably include administration of one or more of a vaccine component (bacterial, yeast, adenovirus) targeting the HIV gag (poly) protein or gp120, NK/CAR-T cells (targeting CD2, CD20, or CD32), and BNAbs (broadly neutralizing antibodies).

Examples

Figure 3:
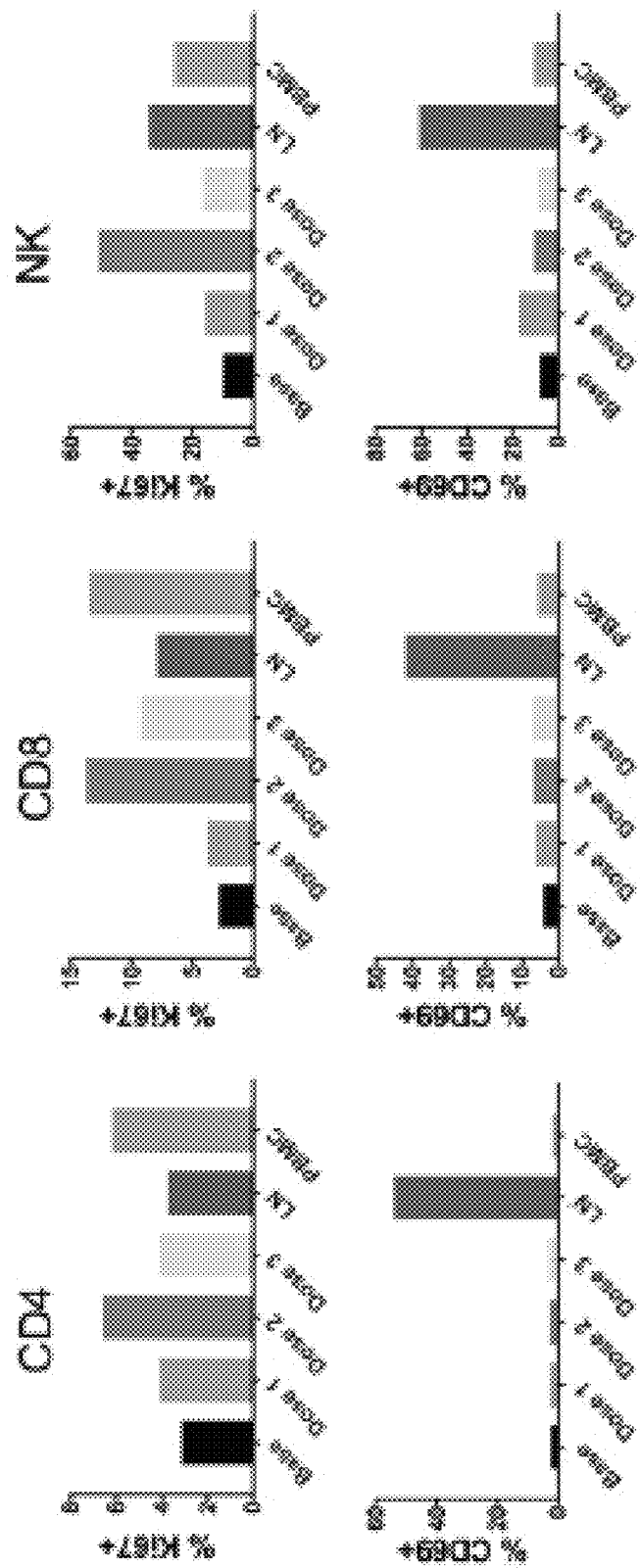
FIG. 3 is a graph depicting exemplary results for stimulation of selected immune competent cells with ALT-803.

ALT-803 stimulation of immune competent cells: As can be readily seen from FIG. 3, ALT803 significantly increases activity of CD4+ T cells, CD8+ T cells, and NK cells. FIG. 3 depict proliferation (Ki67) and activation (CD69) of CD4, CD8, and NK cells after each dose. Base=baseline/pre-dose 1. Dose 1 is 24 hours after the 1st dose. Dose 2 is 24 hours after the 2nd dose. Dose 3 is 24 hrs after the 3rd dose. LN and PBMC were obtained 48 hrs after the 3rd dose. Flow data was obtained from frozen samples at each of the time points indicated.

Figure 4:
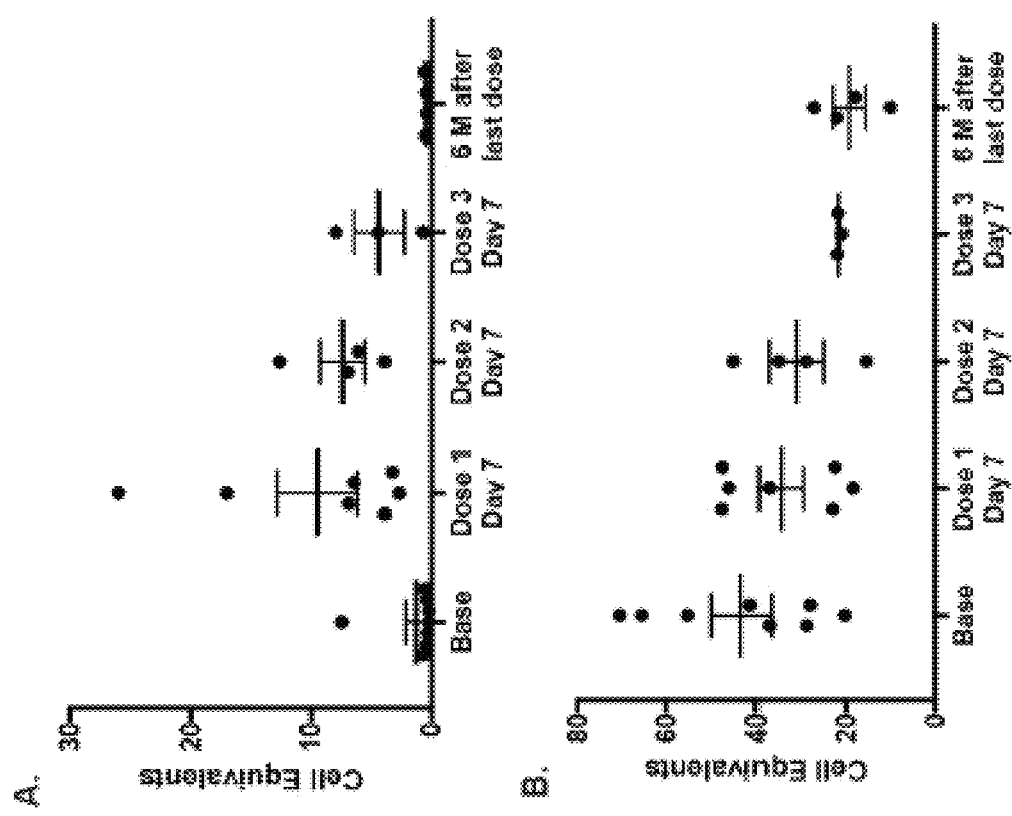
FIG. 4 is a graph depicting mean frequency and SEM of HIV transcription events in 8 participants before and after receiving (A) ALT-803 or (B) Concanamycin A stimulation.

Viral protein expression: FIG. 4 shows mean frequency and SEM of HIV transcription events in 8 participants before and after receiving (A) ALT-803 or (B) ConcanamycinA stimulation. A Next Generation Sequencing (NGS)-based protocol, called EDITS (Envelope Detection by Induced Transcription-based Sequencing), was used to measure inducible cell-associated HIV RNA. Sequences of envelope were detected using a nested PCR on $1.25 \times 10^6$ resting memory cells from aviremic HIV-1-infected subjects before and after ConA stimulation.

Broadly neutralizing antibodies to elicit cell killing by binding of antibodies to latent infected cells: The inventors assessed the breadths and potencies of bNAbs against 36 viruses reactivated from patient CD4+ T-cells, using paired neutralization and infected-cell binding assays. Single antibody breadths ranged from 0-64% for neutralization ($IC_{80}$<10 µg/ml) and 0-89% for binding, with two-antibody combinations reaching 0-83% and 50-100%, respectively. Infected-cell binding correlated with virus neutralization for most antibodies (e.g. 3BNC117, r=0.87, p<0.0001). In short, ADCC assays with primary HIV-infected CD4+ T-cells using either haNK or freshly isolated PBMC NK cells were used. The inventors observed a strong direct correlation between antibody binding and ADCC for both types of NK cells. Notably, a similar relationship was observed for haNKs and fresh NK cells, although with higher overall killing by the haNKs. Among other neutralizing antibodies, especially contemplated antibodies include PGT121, 10-1074, 10E8, 10E8v4-V5R-100cF, 2F5, 2G12, 3BNC117, CAP256.VRC26.25, N6, PG9, PGDM1400, PGT121, VRC01, & VRC07-523, VRC07 523-LS, 3BNC117-LS, 10-1074-LS, & CAP256-VRC26.25-LS, each of which may be used alone or in combination with other therapeutic entities, and especially with ALT-803, as is further described in more detail below.

Figure 5:
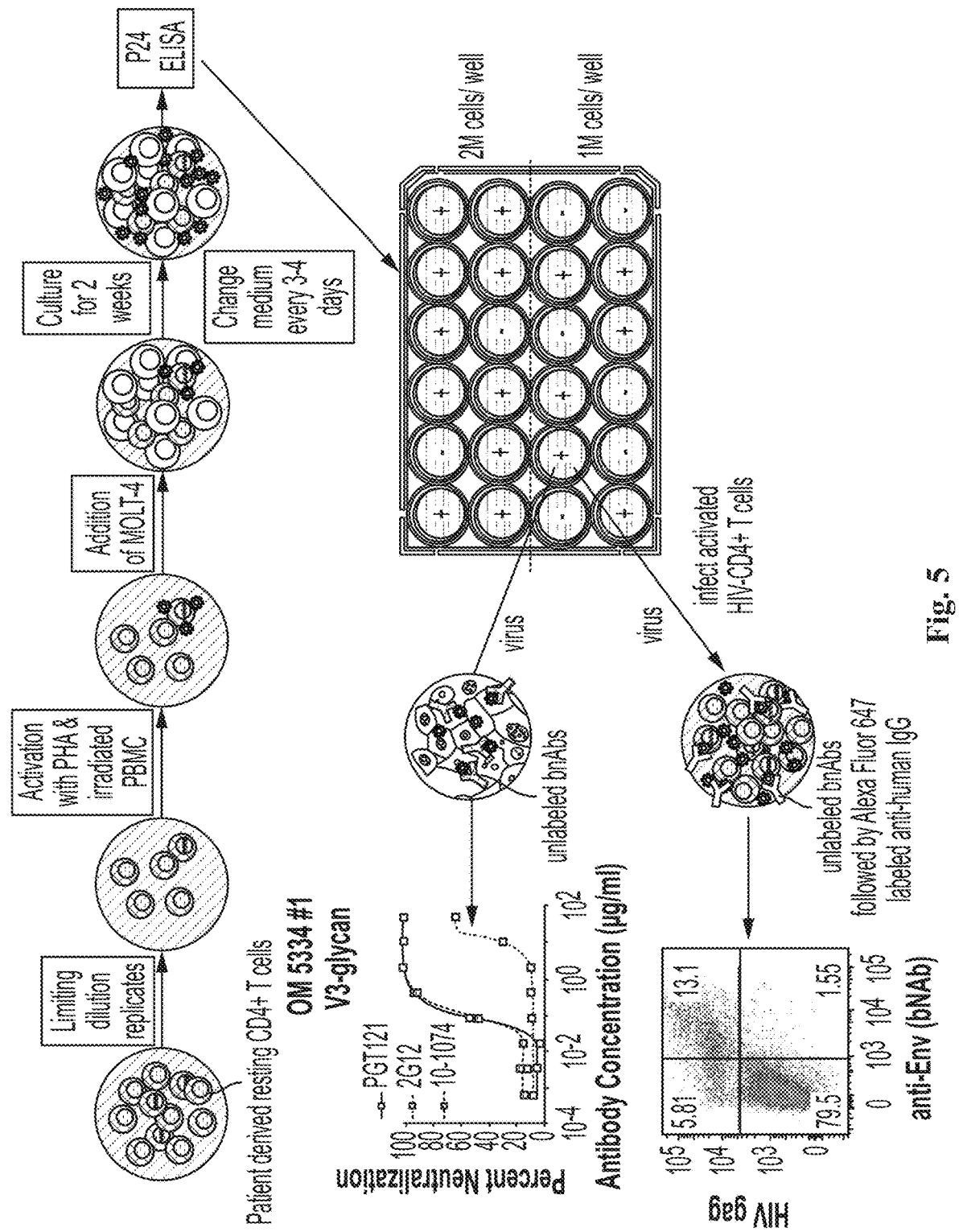
FIG. 5 is a schematic illustration of a quantitative viral outgrowth assay. Here, assays were performed using $CD4^+$ T-cells from ARV-suppressed study participants. Virus was isolated from HIV-$p24^+$ wells at a dilution where <50% of wells were positive. A portion of the supernatants from each of these wells was used directly to assess virus neutralization using a TZM-bl assay. Another portion was used to infect activated primary $CD4^+$ T-cells. Binding of bNAbs to these infected cells was assessed by flow cytometry, co-staining with CD4 and HIV-Gag to identify infected cells.

More particularly, the inventors assessed in parallel virus neutralization and infected primary CD4+ T-cell binding of bNAbs against a panel of 36 viruses that were reactivated from the latent reservoirs of 8 ARV-treated individuals in quantitative viral outgrowth assays (QVOA) (see schematic, FIG. 5). The inventors defined the intra- and inter-patient breadths and potencies of both neutralization and infected cell binding activity of these bNAbs against reactivated reservoir viruses from a geographically localized population of clade B infected individuals. For all bNAbs that demonstrated appreciable neutralizing activity, this correlated closely with infected cell binding.

Figure 6A:
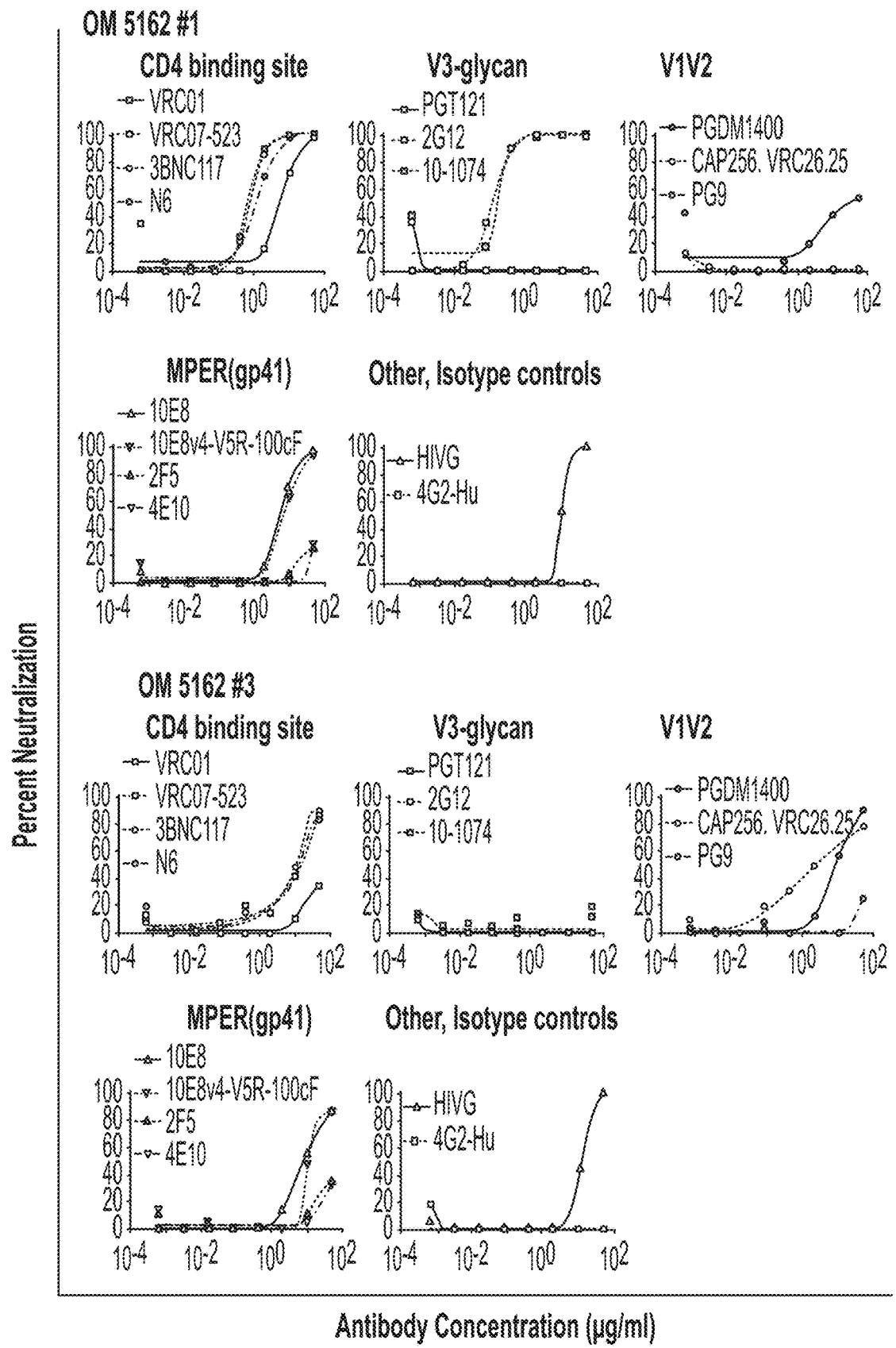
Figure 6B:
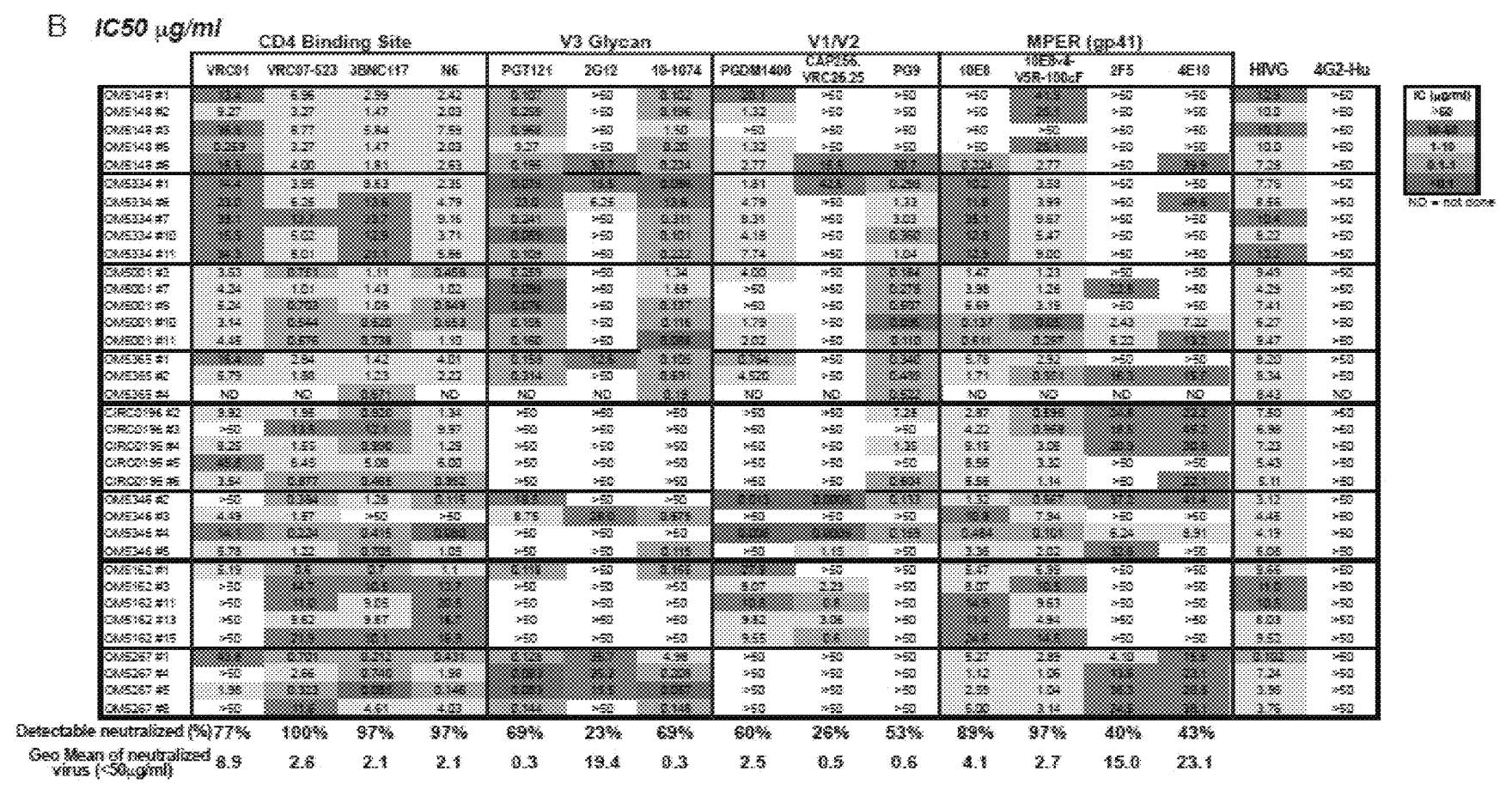

Virus Neutralization Profiles of bNAbs and bNAb Combinations Against Reactivated Reservoir Viruses: To test the ability of bNAbs to neutralize reservoir virus, the inventors obtained a panel of 14 bNAbs that are currently being developed for clinical use in humans and categorized these by their targeted epitope. The inventors measured the neutralizing activities of these bNAbs against 36 viral isolates that had been reactivated from the latent reservoirs of 8 individuals from limiting dilution quantitative viral outgrowth assays (QVOA) (FIG. 6A). The V3-glycan-specific bNAbs PGT121 and 10-1074 and the V1V2-specific bNAb PG9 exhibited potent but relatively narrow activity, exhibiting detectable neutralization (IC50<50 µg/ml) of 53-69% of viruses, with geometric mean IC50 values ranging from 0.3-0.6 µg/ml (FIG. 6B). In contrast, the CD4 binding site (CD4bs)-specific antibodies VRC01, VRC07-523, N6 and 3BNC117, as well as the MPER-targeting antibody 10E8 exhibited broad activity, with a detectable neutralization 77-100% of viruses (IC50<50 µg/ml), but with substantially higher IC50 values (geometric mean IC50 between 2.1-8.9 µg/ml) (FIG. 6B). These trends parallel previous reports using pseudovirus assays, which also observed that CD4bs antibodies and 10E8 were generally much broader but less potent than V3-glycan and V1V2 apex antibodies. In the current experiment, CAP256.VRC26.25 only neutralized 9 of 36 reactivated reservoir viruses (26%) with a detectable IC50 (IC50<50 µg/ml) (FIG. 6B). Because CAP256.VRC26.25 has been reported to preferentially neutralize subtype C, and the QVOA viral isolates tested here are all subtype B, the low neutralization breadth the inventors observed is compatible with published data. One exception to the general agreement between the data and those from published pseudovirus panels was for 2G12 which has been shown to potently neutralizes subtype B viruses in published pseudovirus panels, but the inventors observed only weak neutralization in the assays, with only three viruses reaching 80% neutralization.

Figure 6C:
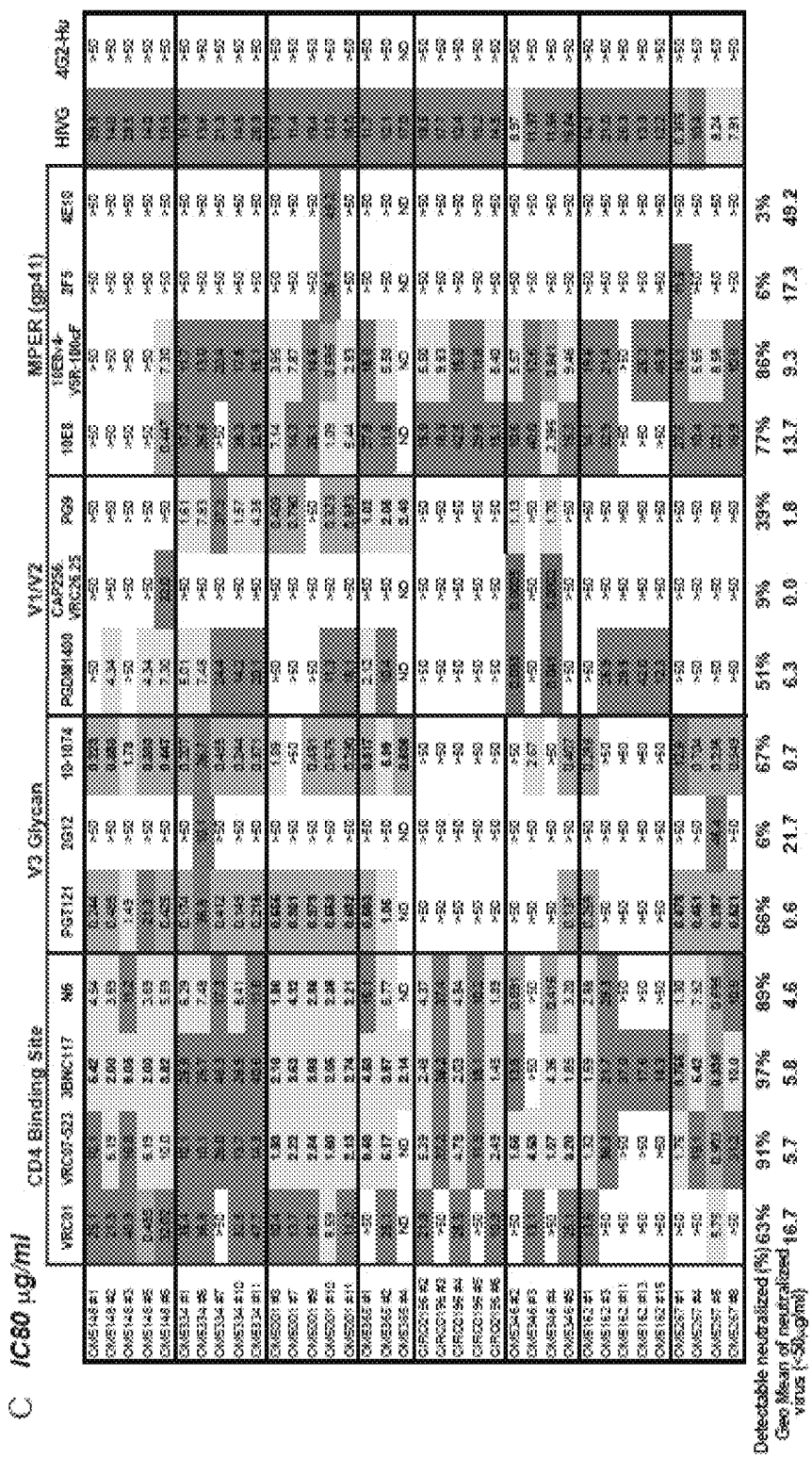

The inventors frequently observed high degrees of similarity in neutralization sensitivities within an individual's viral quasispecies, consistent with genetic relatedness. For example, the five viral isolates from CIRC1096 were all sensitive to neutralization by CD4bs and MPER antibodies, but resistant to V3-glycan and V1V2 antibodies (FIG. 6B-6C). Exceptions to this, however, were not uncommon. For example, for the four QVOA viruses from OM5346, two of these viruses (#2 and #4) were highly sensitive to V1V2 antibodies (PG9, CAP256-VRC26.25, PGDM1400) and resistant to V3-glycan antibodies (PGT121, 10-1074 and 2G12) whereas virus #3 exhibited the opposite sensitivity profile (FIGS. 2B & C). Overall, of the 112 study participant/bNAb combinations (8 participants×14 bNAbs) there were only 14 cases where a single bNAb provided coverage of each of the viral isolates tested from a given participant (IC80<10 µg/ml, FIG. 6C in Bold).

Figure 6D:
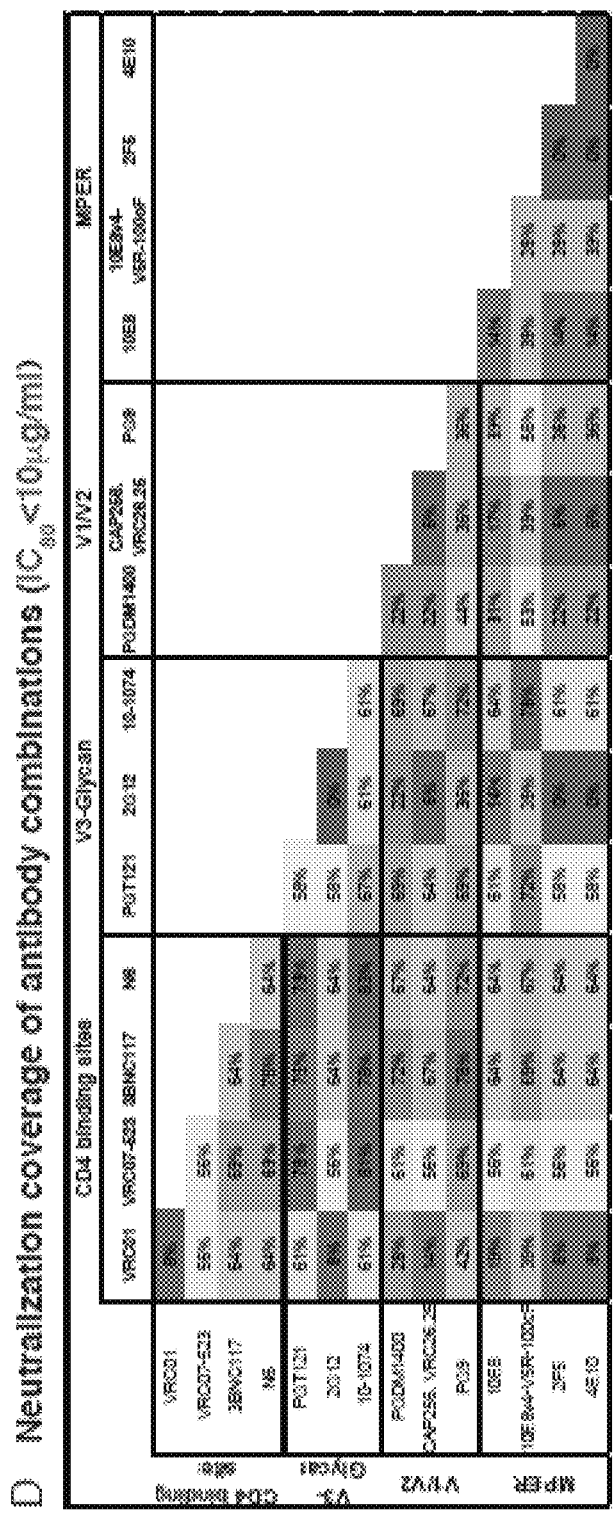

Given the limitations observed above in the breadths of coverage and potential escape of any single bNAb, it is likely that any clinical intervention would require combinations of multiple bNAbs to be effective. The inventors therefore calculated the summed breadths of all combinations of two of the bNAbs tested in this study. The inventors determined breadth coverage by using an IC80<10 µg/ml as the cut-off for the geometric mean sensitivity of the quasispecies based on the previous demonstration that this concentration correlated with reduction in viremia in bNAb-treated clinical trial subjects. The combination of N6 with 10-1074 showed the greatest breadth of coverage, at 83% (IC80<10 µg/ml) (FIG. 6D), followed by the combination of VRC07-523 and 10-1074, which displayed an IC80<10 µg/ml for 81% of the reservoir virus isolates. Several antibody combinations displayed an IC80<10 µg/ml for 78% of the reservoir virus isolates: N6 and PGT121, VRC07-523 and PGT121, 3BNC117 and 10-1074, 3BNC117 and PG9, 10E8v4-V5R-100cF and 10-1074. Thus, two antibody combinations are able to provide broad neutralization coverage of reactivated reservoir viruses at an IC80<10 µg/ml for this geographically discrete clade B infected population.

Figure 7A:
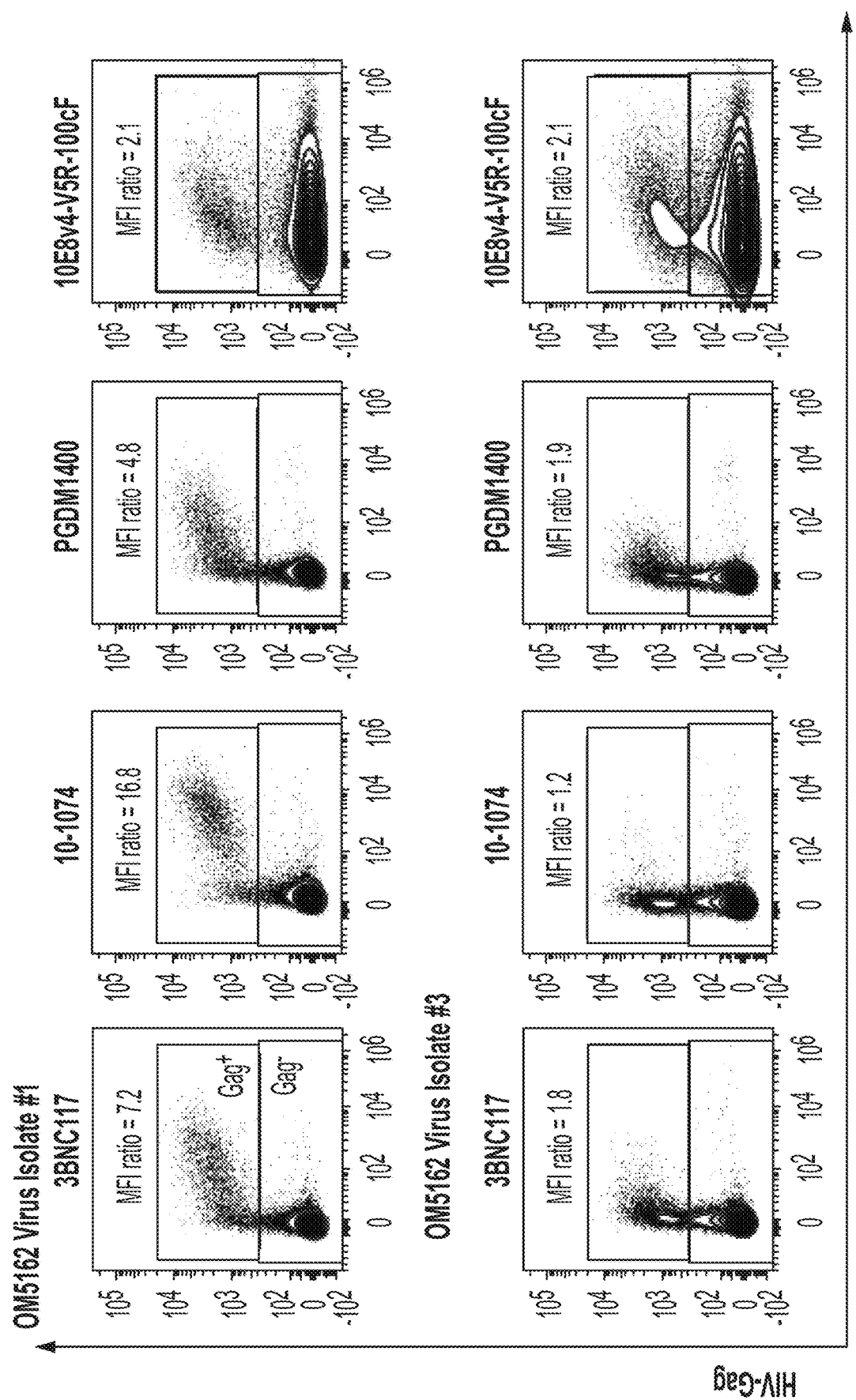

Infected-Cell Binding Profiles of bNAbs and bNAb Combinations Against Reactivated Reservoir Viruses: The inventors next measured the binding of bNAbs to primary CD4+ T-cells infected with the same reservoir virus isolates that had been assessed for neutralization. Activated CD4+ T cells from HIV-uninfected donors were infected with reactivated reservoir viruses and stained with unconjugated bNAbs, followed by Alexa Fluor 647 anti-human IgG secondary antibody. These samples were also stained with HIV Gag to identify infected cells. The inventors used a Median Fluorescence Intensity (MFI) ratio to quantify specific bNAb binding activity to infected cells [MFI ratio=(MFI of bNAb staining in HIV-Gag+ cells)/(MFI of bNAb staining in HIV-Gag− cells)] (FIG. 7A). Since the inventors had already established the geometric mean IC80 neutralization values for each virus, the inventors opted to test infected-cell binding at two concentrations for each antibody: i) 5 μg/ml—selected based on titration experiments (data not shown) ii) IC80 neutralization concentrations for each antibody (values are indicated below the table in FIG. 6C).

Figure 7B:
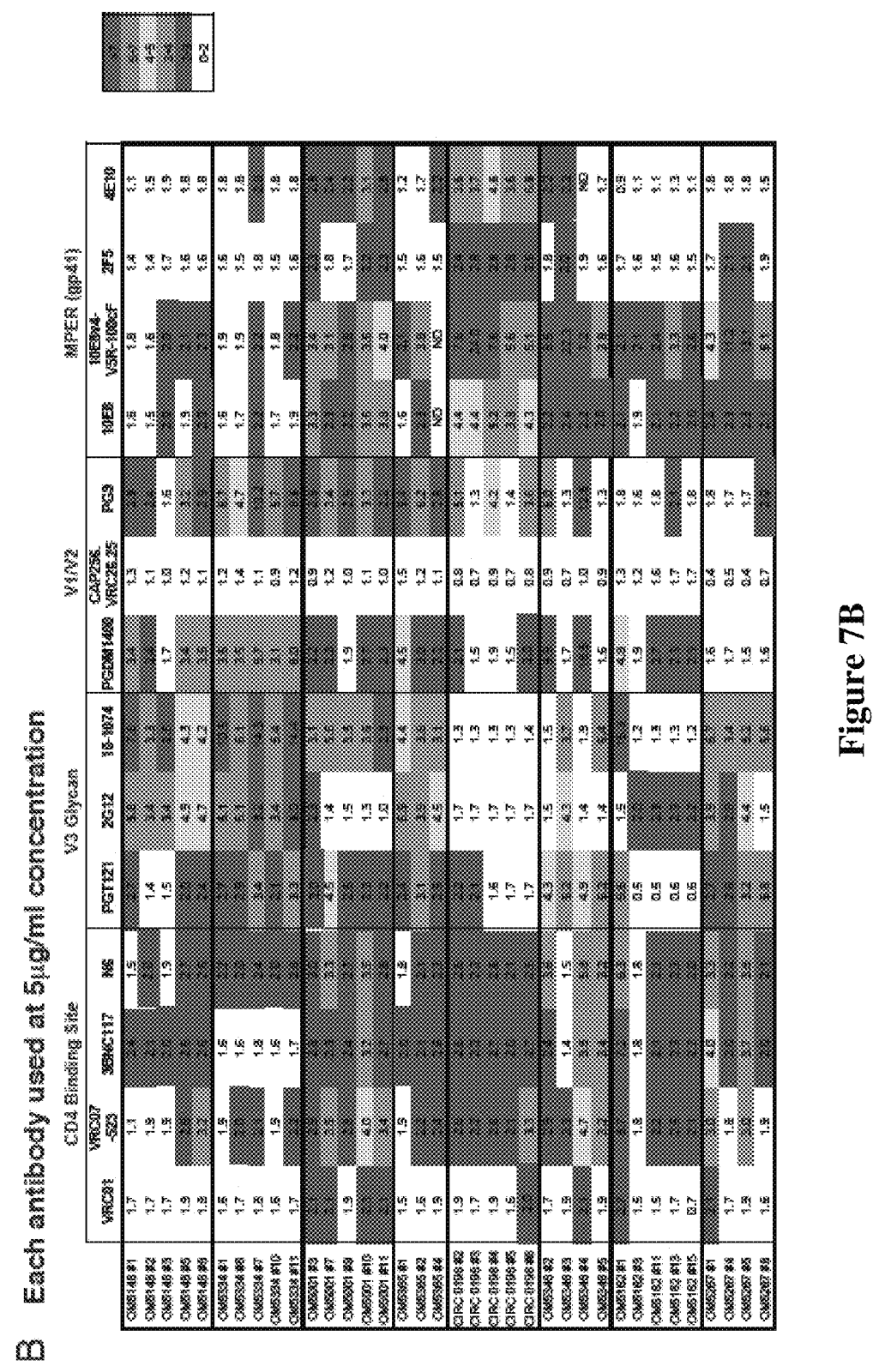
Figure 7C:
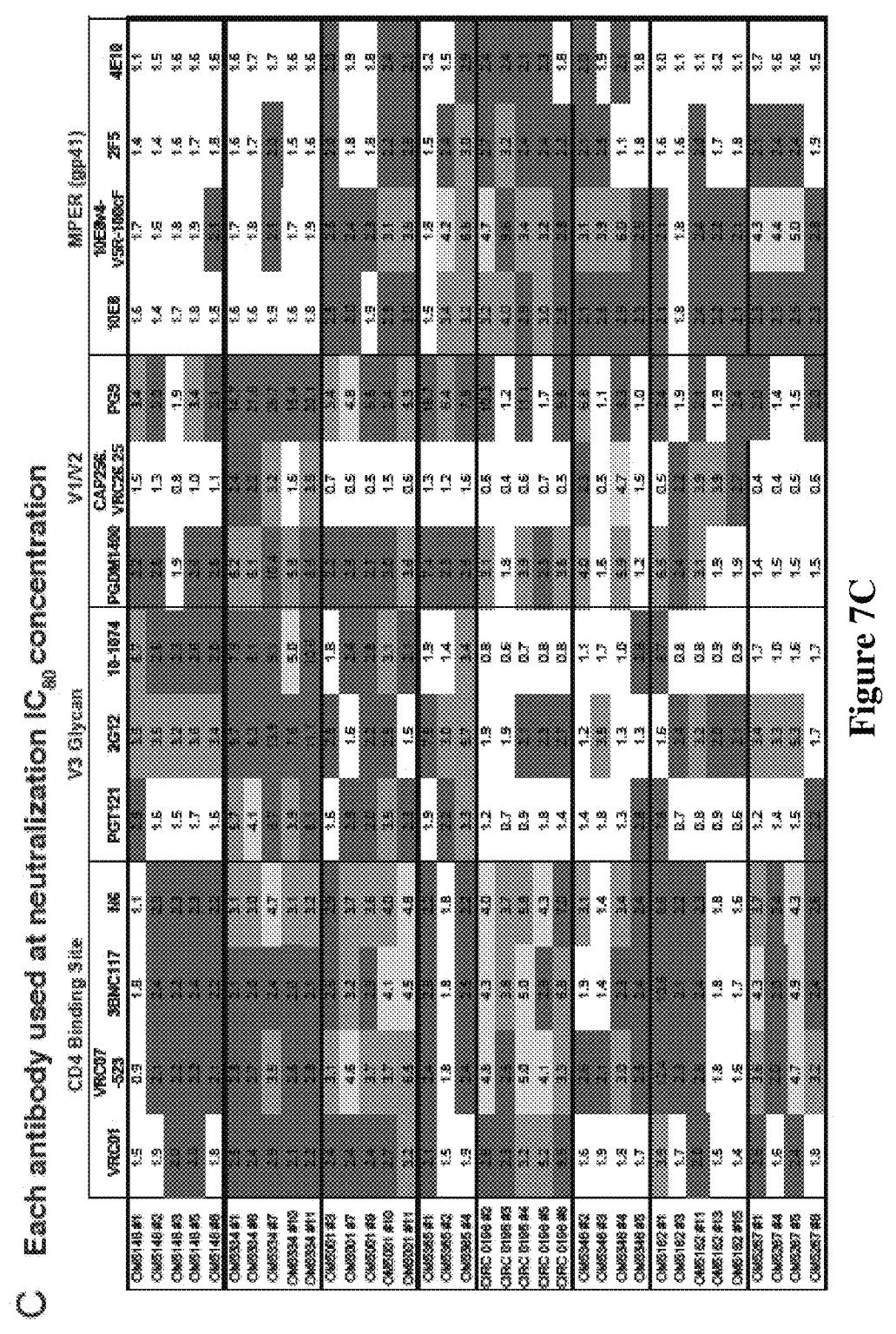
Figure 7D:
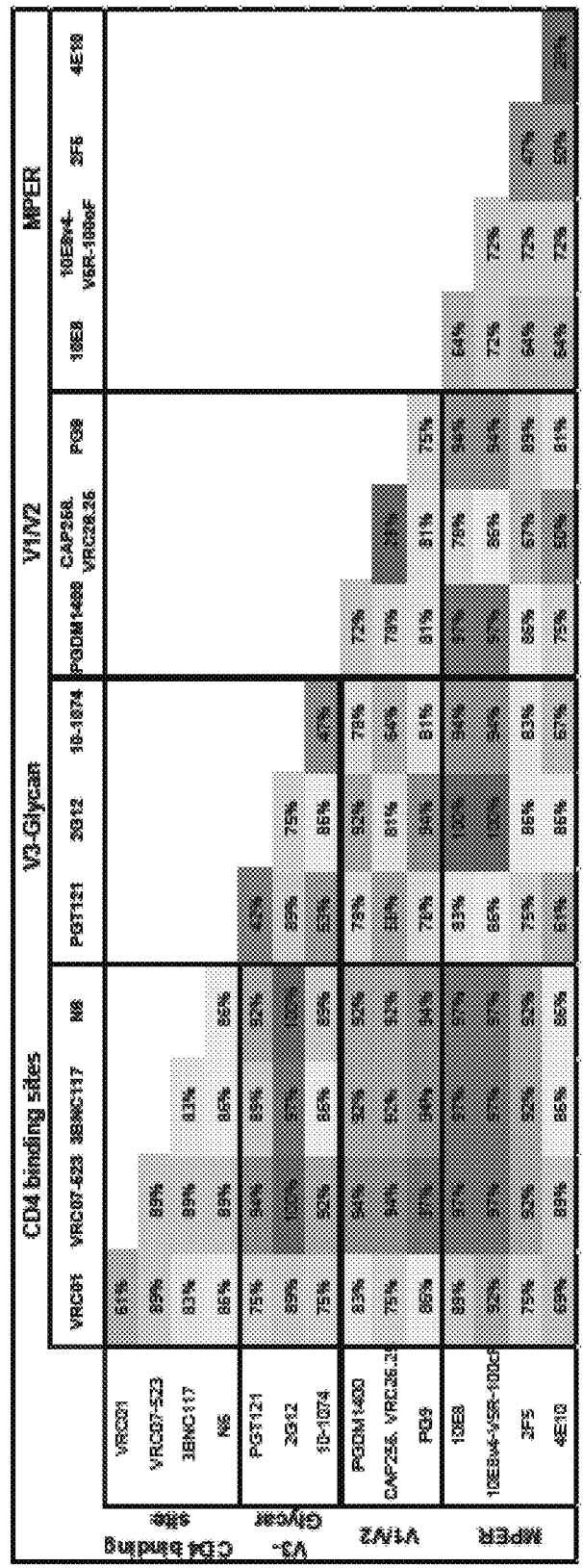

In order to establish breadth, the inventors defined binding as a MFI ratio>2. In general, with the exception of VRC01, CD4bs Abs exhibited superior breadths of infected-cell binding, covering 83-89% of reservoir isolate viruses when tested at the neutralization IC80 concentrations (FIGS. 7C-7D). The binding potencies of CD4bs were relatively modest, however, with most exhibiting MFI ratios of between 2-4 (FIGS. 7B-7C). The V3-Glycan antibodies PGT121, 2G12, and 10-074 exhibited more limited breadths as compared to CD4bs antibodies, but showed substantially higher levels of specific binding to cells infected with susceptible viruses, with many MFI ratios exceeding 5. Sensitivity/resistance profiles were generally related for different viral isolates from the same individual, e.g. 10-1074 bound strongly to all isolates from 5/8 participants (FIG. 7B), but exhibited a lack of binding to all viruses from CIRC0196 (at both concentration). Intra-patient variability was observed, however, for example with 1 out of 5 viruses from OM5162 exhibiting high sensitivity to 10-1074 and the remaining 4 exhibiting resistance. With the exception of CAP256.VRC26.25 (which is predominately clade C specific), the V1/V2 bNAbs showed potent binding activity, particularly in the case of PG9 which, at IC80 concentration, showed high levels of specific binding to 16 of 36 reservoir viruses with an MFI ratio greater than 4 (FIG. 7C). Infected cell binding of MPER-specific antibodies varied: 10E8v4-V5R-100cF, a version of 10E8 optimized for increased solubility and potency45, at 5 μg/ml, bound to 30 of 36 isolates with high-level binding for 13 these (MFI ratios>4). However, 10E8 and 10E8v4-V5R-100cF also showed substantial binding to uninfected bystanders (Gag-population) (see FIG. 7A, left panel for representative staining). In contrast, the MPER-specific bNAbs 2F5 and 4E10 exhibited generally narrow and weak binding of reservoir viral isolates (FIGS. 3B & C). Of note, virus #1 from patient OM5162 showed a highly distinct bNAb binding profile as compared to other isolates from the same individual: it was bound strongly by antibodies VRC07-523, 3BNC117, N6, PGT121, 10-1074 and PGDM1400, whereas other autologous viral isolates were bound weakly if at all by these bNAbs. Similarly, viruses from OM5346 showed intra-individual diversity in binding to V3-glycan-specific bNAbs too, as shown PGDM1400 and PG9 bound robustly to viruses #1 and #3 (MFI ratio>6), while no binding was observed for viruses #2 and #4 (FIGS. 7B and 7C). The data indicate both intra- and inter-individual variability in binding to cells infected with reservoir viral isolates, highlighting the limitations of using any single antibody in a therapeutic.

Achieving broad coverage of viral reservoir isolates in a population is likely to require combinations of at least two bNAbs. To assess this in the current population, the inventors calculated the binding coverage of all possible two antibody combinations using the binding data obtained with the neutralization IC80 antibody concentration (FIG. 7D). All CD4bs (excluding VRC01) antibodies, when combined with 2G12 or V1/V2 antibodies or MPER antibodies (except for 4E10), reached>92% coverage. Notably, the combinations of 2G12 with VRC07-523 or N6, or 10E8 or 10E8v4-V5R-100cF reached 100% coverage, however, as previously mentioned, 10E8v4-V5R-100cF showed a high level of bystander binding in the in vitro assays. 3BNC117+2G12 and VRC07-523+PG9 reached 97% coverage, thus representing promising combinations for targeting reactivated clade B reservoir viruses (FIG. 7D).

With respect to the effects of the different concentrations of antibodies tested on binding, 10E8v4-V5R-100cF exhibited generally more favorable binding profiles (MFI ratios) at 5 μg/ml, due to a reduction in the background binding that was observed at its IC80 concentration of 9.3 μg/ml. In contrast, PG9 showed a lack of background binding even at 5 μg/ml, and thus displayed favorable binding profiles at this higher concentration (FIGS. 7B and 7D).

bNAbs Exert Differential Binding to Populations of Early (Gag+CD4+) Versus Late (Gag+CD4-) HIV-Infected Cells: The infection of a cell by HIV results in the progressive, and almost complete, loss of surface CD4 expression, through the concerted actions of Nef, Vpu, and Env. Thus, in short-term in vitro infections of activated CD4+ T-cells, Gag+CD4− cells represent a later stage of infection than their Gag+CD4+ counterparts (which have not yet down-regulated CD4). Cell-surface CD4 has been shown to affect the conformation of Env in cis (on the same cell), for example by inducing gp120 shedding and the exposure of gp41 stumps. The infected-cell binding data-set described above gave us the opportunity to test for evidence of such effects in these primary CD4+ T-cells infected with reactivated reservoir viruses.

Figure 8A:
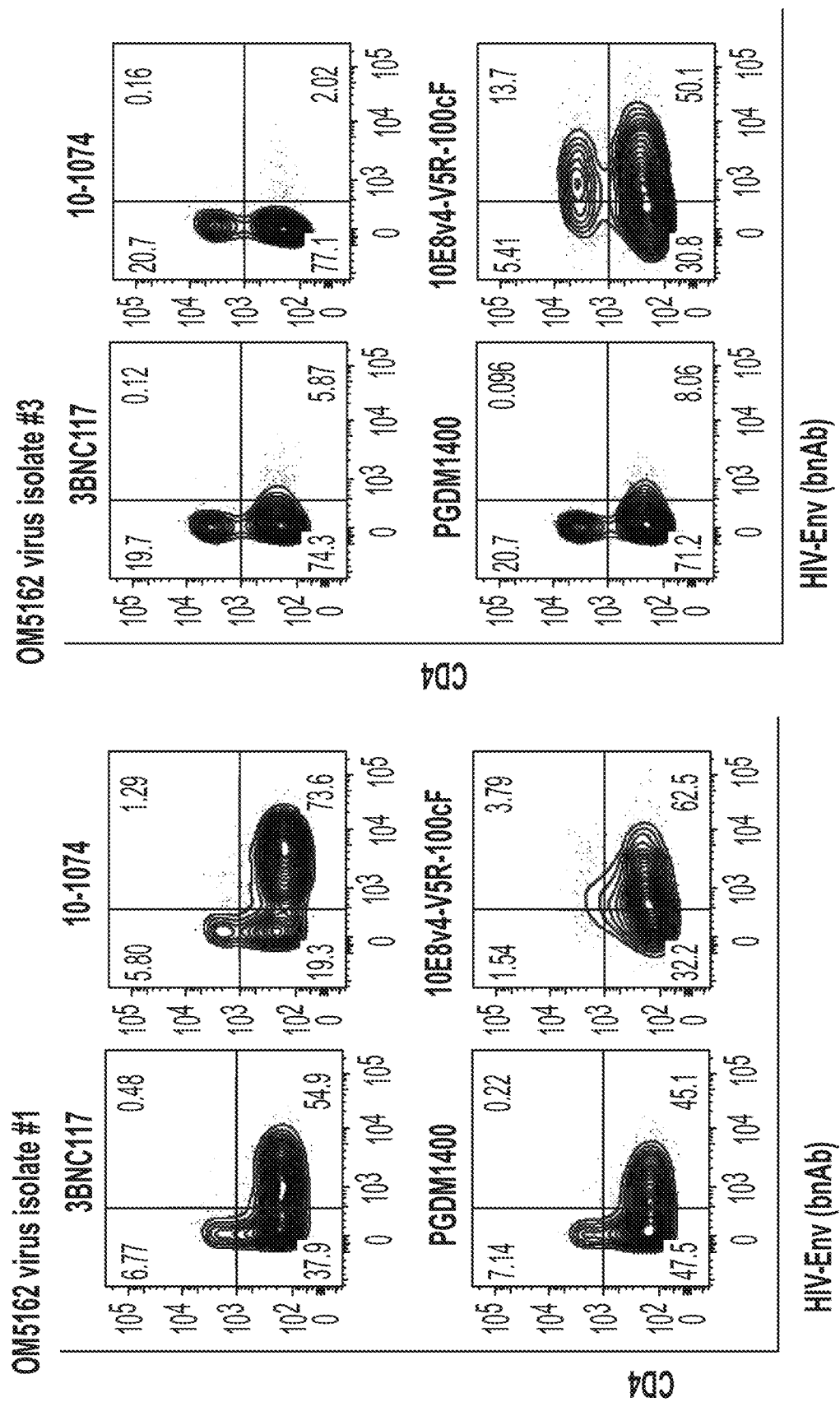
FIGS. 8A & 8B are exemplary results showing that $Gag^+CD4^-$ population represents the specific binding to HIV Env. (8A) Representative flow plots gated on live/$CD3^+$/$HIV^-Gag^+$ (all infected cells) showing differential bNAb binding to $CD4^-$ (early infected) and $CD4^-$ (late infected) populations. The numbers show the percentages of cells in each quadrant and indicate that for 3BNC117 and 10-1074 most bNAb binding occurs with the $CD4^-$ population. (8B) Summary data for the analysis represented in panel A, showing paired comparisons of MFI ratios between $CD4^+$ and $CD4^-$ populations. MFI ratio is defined as (MFI of bNAbs in $Gag^+CD4^+$)/(MFI of bNAbs in $Gag^-$) or (MFI of bNAbs in $Gag^+CD4^-$)/(MFI of bNAbs in $Gag^-$). The numbers indicate fold differences (mean of Gag⁺CD4⁻MFI ratio)/(mean of Gag⁺CD4⁺MFI ratio).
Figure 8B:
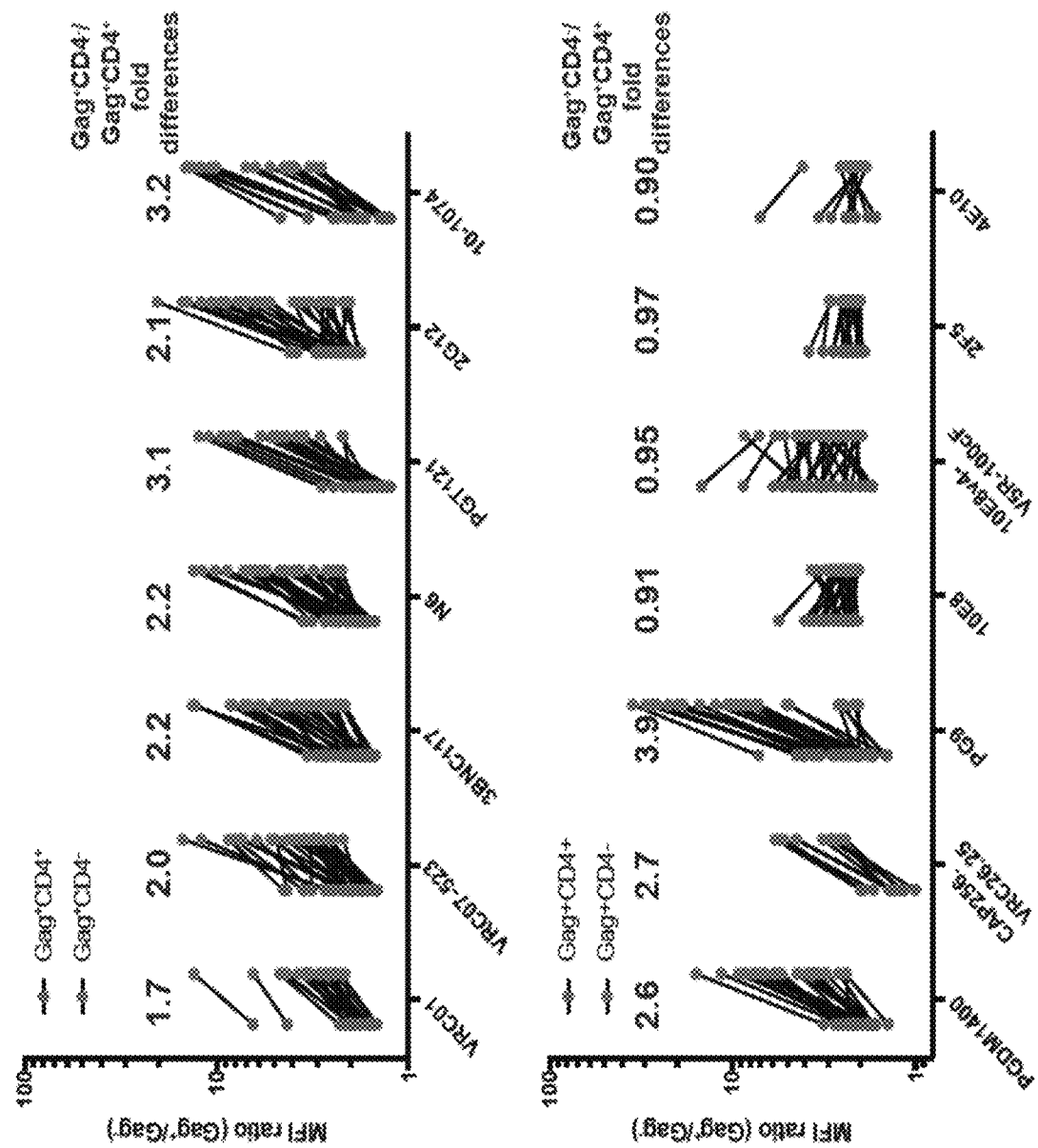

The inventors than assessed whether differential binding of bNAbs to early (Gag+CD4+) versus late (Gag+CD4−) infected cells was present in the assays. Upon gating on viable HIV-infected cells (lymphocytes, live cells, CD3+, HIV-Gag+), the inventors observed clear distinctions, with some bNAbs, such as 3BNC117, 10-1074, and PGDM1400 showing preferential binding to late infected cells (CD4−) (FIG. 8A, upper panels), and others, such as 10E8v4-V5R-100cF showing similar binding to early and late populations (FIG. 8A). To test this systematically, the inventors selected the samples which showed binding (all Gag+/Gag− MFI ratio>2) when tested at neutralization IC80 concentrations and compared infected cell binding (MFI ratios) of bNAbs in the Gag+CD4+ versus Gag+CD4− populations (FIG. 8B). In addition, the inventors calculated fold differences between these early and late infected populations=(Geometric Mean MFI ratio of Gag+CD4−)/(Geometric Mean MFI ratio of Gag+CD4+). The inventors observed that all gp120-specific bNAbs exhibited higher levels of binding to late-infected populations than to matched early-infected populations (Fold differences: 1.7-3.9, FIG. 8B). In contrast, each of the gp41-specific bNAbs exhibited similar or slightly higher levels of binding to early-versus late-infected populations (Fold differences: 0.90-0.97, FIG. 4B). Since Env is expressed at higher levels in late-infected cells and therefore higher binding to late-infected cells would be expected, this result is consistent with preferential binding of gp41-specific bNAbs to the conformation of Env present on early-infected cells. In addition, these results are consistent with the idea that not only the amount of Env but also the presence of CD4 on the surface on infected cells influences bNAb binding profiles. One implication is that the binding data presented in FIG. 7—which was generated based on total Gag+ cells—over-represents binding to early-infected cells for gp120-specific antibodies and under-represents binding to late-infected cells. Data calculated based only on the late-infected populations show a substantially intensified binding profile for most of the bNAbs used in this study—most notably for the CD4bs bNAbs and PG9. A second implication is that cellular infection dynamics may impact the ability to detect relationships between infected-cell binding and virus neutralization. For example, if virus 1 replicated with faster kinetics than virus 2, and thus had a greater proportion of Gag+CD4− versus Gag+CD4+ cells, then this would skew bNAb binding profiles in a way that was not intrinsic to the Env itself. To account for this, the inventors assessed these relationships based on both total Gag+ cells and on only the Gag+CD4− late infected populations (below).

Virus Neutralization Correlates with Infected-Cell Binding for most bNAbs: The breadths and potencies of neutralizing activity of bNAbs against diverse HIV isolates have been extensively studied. In contrast, relatively few studies have assessed breadths and potencies of infected-cell binding, which is an important pre-requisite for ADCC. Efforts to harness bNAbs to direct ADCC against infected cells would therefore benefit from an understanding of the degree to which infected cell binding can be inferred from neutralizing activity against a given virus. The paired binding and neutralization data sets allowed us assess this using a number of analytic approaches in regards to both concentrations of bNAbs used for binding assays and to stage of infection of target cells. With respect to bNAb concentrations, binding to infected cells was assessed for each bNAb at 5 μg/ml, and at the geometric mean IC80 neutralization concentration of that antibody against the panel of reservoir viruses. For the latter, this meant that some antibodies were tested at >5 μg/ml (ex. 4E10 at 49.2 μg/ml), while other antibodies were tested at substantially lower concentrations (e.g. PGT121 at 0.6 μg/ml) (Geo Mean IC80 concentrations are given below the heat-map in FIG. 6C). This approach thus seeks to normalize for intrinsic differences in avidity between different bNAbs. With respect to stage of infection of target cells, the inventors separately tested for correlations between neutralization IC80 and binding to either total infected cells (Gag+) or to late-infected cells (Gag+CD4−), based on the differential binding patterns described above. Of these, the most appropriate method for assessing the relationship between binding and neutralization likely depends on the question being asked. Importantly, however, the relationships that the inventors observed, as described below, turned out to be conserved across these different approaches.

Figure 9A:
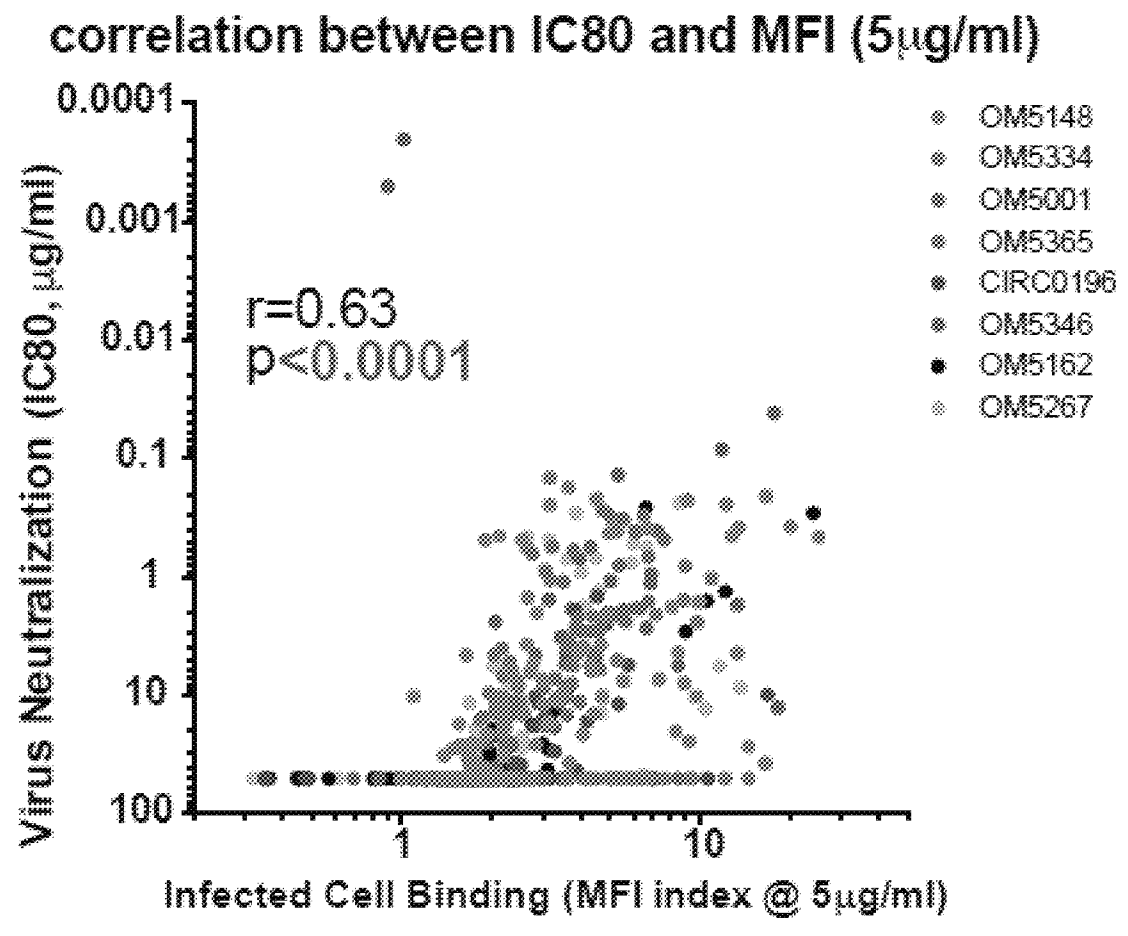
Figure 9B:
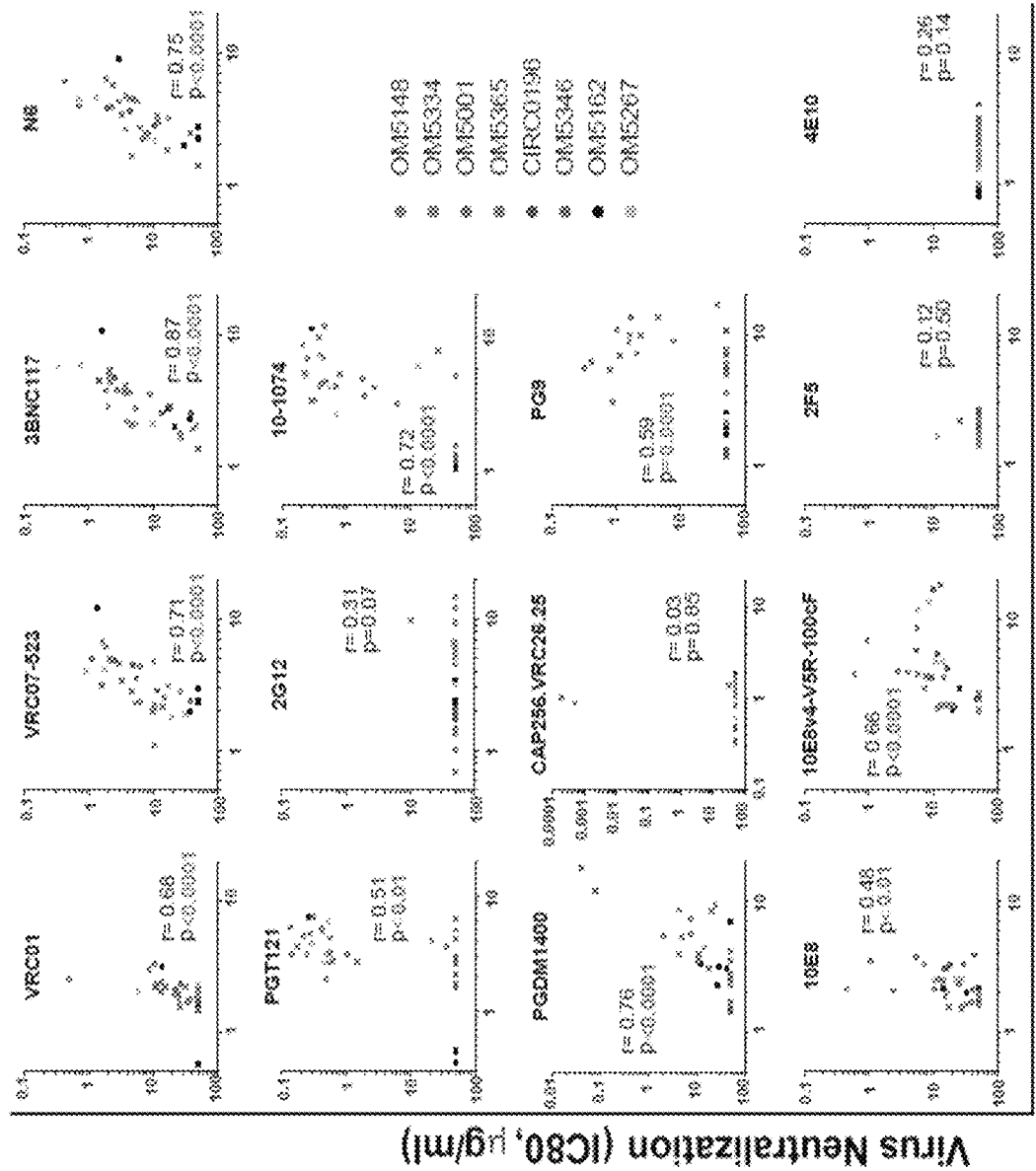

The inventors first tested for correlations between neutralization IC80 concentration and the level of binding (MFI ratio) at 5 μg/ml bNAb concentrations. As is described above, since cells in early versus late stages of HIV infection exhibit differential bNAb binding profiles, replication dynamics have the potential to impact overall assessments of binding. In order to increase the ability to discern Env-intrinsic relationships between binding and neutralization the inventors therefore limited this initial analysis to the late-infected (Gag+CD4−) population. When all antibodies were considered together, the inventors observed a significant, direct correlation between virus neutralization and infected cell binding (p<0.0001, r=0.63) (FIG. 9A). For each of the bNAbs that showed appreciable neutralizing activity (VRC01, VRC07, 3BNC117, N6, PGT121, 10-1074, PGDM1400, PG9, 10E8, and 10E8v4-V5R-100cF) the inventors observed significant direct correlations between neutralizing activity and infected-cell binding (FIG. 9B). The antibodies 2F5 and CAP256.VRC26.25 showed little in the way of either neutralization or binding, precluding the possibility of detecting a relationship between these factors.

2G12 and, to lesser extent, 4E10 were notable outliers as they showed appreciable binding capacity to many of the viruses in this panel, but very little corresponding neutralizing activity. This lack of potent neutralization activity is inconsistent with data from pseudovirus assays, but in agreement with previous data using virus produced from T-cells, suggesting that 2G12 sensitivity is particularly tied to the source of virus.

Correlations between neutralization IC80 concentrations and binding as measured by other approaches are presented as follows: i) binding of antibodies tested at 5 μg/ml concentrations to total infected population (all Gag+); ii) binding of antibodies tested at IC80 neutralization concentrations to late infected population (Gag+CD4−); iii) binding of antibodies tested at IC80 neutralization concentrations to total infected population (all Gag+). Correlation coefficients varied considerably across these different analyses, with different approaches yielding stronger correlations for different bNAbs, e.g. for 3BNC117: Spearman's r=0.82 for 5 μg/ml total Gag+ vs Spearman's r=0.60 for IC80 concentration total Gag+; for PGT121: Spearman's r=0.47 for 5 μg/ml total Gag+ vs Spearman's r=0.71 for IC80 concentration total Gag+. Overall, however, each of the antibodies that exhibited a significant correlation by one analytic approach also exhibited significant correlations by the other three approaches, and vice versa for those lack significant correlations. Thus, the ability of a bNAb to neutralize a given virus is strongly correlated with its ability to bind to a corresponding infected cell. In these in vitro assays, this correlation was robust enough to be observed with or without controlling for avidity of a given bNAb or for infection dynamics.

Methods: The inventors used a panel of broadly neutralizing antibodies to HIV (bNAbs): CD4 binding sites antibodies (CD4bs)—VRC01, VRC07-523, 3BNC117, N6; V3-Glycan antibodies—PGT121, 2G12, 10-1074; V1/V2 antibodies—PGDM1400, CAP256.VRC26.25, PG9; MPER antibodies—10E8, 10E8v4-V5R-100cF, 2F5, 4E10; and a positive control antibody HIV-IG and a negative control antibody 4G2-Hu for neutralization assays. Antibodies 10-1074, 2G12, and control antibody HIV-IG were obtained through the AIDS Reagent Program, Division of AIDS, NIAID, NIH from Dr. Michel C. Nussenzweig, Polymun Scientific and NABI and NHLBI, respectively. Dr. John Mascola provided antibody proteins 2F5 and 4E10, as well as all other antibody heavy- and light-chain expression plasmids. Antibody plasmids were expressed as full-length IgG1s from transient transfection of 293F cells and purified by affinity chromatography using HiTrap Protein A HP Columns (GE Healthcare).

Quantitative viral outgrowth assay (QVOA): Human CD4 T cells were enriched from the peripheral blood mononuclear cells (PBMCs) (STEMCELL Technologies, 19052), processed from leukapheresis, which were drawn from long-term ARV-treated HIV-infected participants. Cells were diluted into a serial concentration (2 million, 1 million, 0.5 million, 0.2 million and 0.1 million per well), and plated out into 24 well-plates and each concentration would have 12 wells. PHA and irradiated PBMCs were added to reactivate the infected cells and MOLT-4 cells were added on day 2 to amplify the viruses. Media were changed every 3-4 days and p24 ELISA were run on day 14 to measure the amount of virus production.

p24 Enzyme-Linked Immunosorbent Assay: p24 enzyme-linked immunosorbent assay (ELISA) was performed with kit components obtained from National Cancer Institute, NIH. In brief, 96-well high binding microplates (Greiner Bio-One) were coated with capture antibody for overnight, and blocked with 1% BSA solution for overnight. Supernatants from QVOA wells were collected and lysed with 1% x-Triton buffer for 2 hours, followed by transferring to ELISA plates and incubating for 1 hour, 37° C. After 6 times plate washes with microplate washer (BioTek), primary antibody was added. 1 hour incubation later, peroxidase labeled secondary antibody (KPL) were added and incubated for another 1 hour at 37° C. After 6 times washes, TMB substrate (Thermo Fisher) were added and developed for 15 mins, then stopped with stop solution (Biolegend). Absorbance were measured with the SpectraMax i3× Multi-Mode microplate reader (Molecular Device) at OD450 nm and 570 nm, and cut off was set as >2× average of negative control values.

Neutralization assay: Neutralization of QVOA virus samples by mAbs were measured using infection of Tzm-bl cells as described previously. Briefly, p24 protein in each virus sample was quantified by using the AlphaLISA HIV p24 Biotin-Free detection kit (Perkin Elmer, Waltham, Mass.), and input virus was normalized to 5-10 ng/ml for the assay. 10 µl of five-fold serially diluted mAbs from a starting concentration of 50 µg/ml were incubated with 40 µl of replication competent virus samples in duplicate for 30 minutes at 37° C. in 96-well clear flat-bottom black culture plates (Greiner Bio-One). Tzm-bl cells were added at a concentration of 10,000 cells per 20 µl to each well in DMEM containing 75 µg/ml DEAE-dextran and 1 µM Indinavir. Cell only and virus only controls were included on each plate. Plates were incubated for 24 hours at 37° C. in a 5% CO2 incubator, after which the volume of culture medium was adjusted to 200 µl by adding complete DMEM containing Indinavir. 48 hours post-infection, 100 µl was removed from each well and 100 µl of SpectraMax Glo Steady-Luc reporter assay (Molecular Devices, LLC., CA) reagent was added to the cells. After a 10-min incubation at room temperature to allow cell lysis, the luminescence intensity was measured using a SpectraMax i3× multi-mode detection platform per the manufacturers' instructions. Neutralization curves were calculated comparing luciferase units to virus-only control after background subtraction and fit by nonlinear regression using the assymetric five-parameter logistic equation in GraphPad Prism (FIG. 6A). The 50% and 80% inhibitory concentrations (IC50 and IC80, respectively) were defined as the antibody dilution that caused a 50% and 80% reduction in neutralization.

bNAb binding assay: All binding assays were tested with the unconjugated bNAbs. CD4+ T cells were isolated with the Human CD4 T cell enrichment kit (STEMCELL Technologies) and activated with CD3/28 antibodies (Biolegend) for 48 hours. Supernatants collected from QVOA wells (p24+) were used for infection by adding into the activated CD4+ T cells, followed by spinnoculation for 1 hour and 6 days in culture with media change every 3 days. Infection rate was checked on days 3 and 5 post infection. When most of the infection reached>5%, bNAb staining were performed. Cells were collected and washed twice with MACS buffer (DPBS with 2% FBS), and then aliquoted into 96-well plates (1 million cells per well). Unconjugated bNAbs were added according to the outlined wells by diluting to a final concentration of 5 µg/ml or IC80 concentration, which was the Geo Mean of neutralized virus that generated from neutralizing assay, and then incubated in 37° C. for 1 hour. Without washing, the Alexa Fluor 647 labeled secondary antibody (Southern Biotech, 2040-31) was added and incubated at 4° C. for half an hour. After washing twice with MACS buffer, surface antibodies mixture was added: BV786 anti-human CD3 (BD Biosciences, 563800), Pacific Blue anti-human CD4 (BD Pharmingen, 558116) and LIVE/DEAD aqua (Life technology, L34966). 30 minutes later, cells were washed and fixed/permeabilized with Fixation/Permeabilization Solution (BD Bioscience, 554714). Anti-HIV-1 core antigen antibody (KC57-RD1, Beckman Coulter, 6604667) was used to stain intracellular HIV-1 gag protein. After two washes with 1× Perm/Wash buffer, cells were detected by flow cytometry (BD Fortessa X-20), and the data analysis was performed with flowjo v10.

Statistical analysis: Statistical analyses were performed using Prism 7 (GraphPad). Flow data were analized with flowjo v10. The heat-maps were generated with Excel. Correlation between neutralization IC80 and IC80 concentration bNAb binding was using spearman test.

The primary conclusion of the above results is that the ability of a given bNAb to neutralize clinical viral isolates is a strong correlate of its ability to bind to cell-surface Env on primary CD4+ T-cells infected with the same virus. Furthermore, in comparing across a large panel of bNAbs, relative levels of infected-cell binding and virus neutralization continued to correlate—for example, 10-1074 showed both high-level infected-cell binding and potent neutralization compared to VRC01. Thus, the inventors conclude that— with respect to the Fab component of an Ab—the selection of Abs based on broad and potent neutralizing activity is very likely to also select for those that are suitable for infected-cell clearance. Of note, the reciprocal was not always true; with 2G12 exhibiting reasonably potent and broad infected-cell binding, contrasted by a general lack of neutralization of these reservoir-derived primary isolate viruses. Though less strikingly, the MPER-specific bNAbs 2F5 and 4E10 also exhibited appreciable infected-cell binding (similar in breadths and magnitudes to VRC01), but with minimal neutralizing activity. The inventors propose that the differences based on the directionality of this relationship may be related to the differential antigen conformational requirements for these two functions. For a bNAb to neutralize virus, it must bind functional Env trimers present on the surface of cells producing infectious virus. In contrast, an antibody that also binds to nonfunctional envelope proteins, such as gp41 stumps, may bind to infected cells to a greater degree than they mediate neutralization (if they neutralize at all). Thus, virus neutralization is a predictor of infected-cell binding, but the reciprocal relationship does not hold.

While it may be intuitive that virus neutralization would correlate with infected-cell binding, the inventors do not feel that this could have been assumed to be the case without experimental evidence. The conformation of Envs may be affected by differences between the cell-surface vs virion environments, and this variability could impact different viral isolates. For example, in cis interactions between CD4 and Env on the surfaces of infected cells have been shown to induce gp120 shedding, and expose gp41 stumps. This has been reported to enhance infected-cell binding by gp41-specific Abs, while diminishing binding by gp120-specific Abs. Such an effect might differentially impact different viruses—for example, Horwitz et al. reported that the R456K mutation on YU2 gp120 decreased gp120 shedding, which led to less bystander (Gag–CD4+) binding. The data are consistent with these observations, and provide further evidence of cis binding of CD4 modulating the binding of bNAbs to infected-cells. The inventors find gp120-specific bNAbs bind preferentially to cells in a late stage of infection (CD4low) while gp41-specific bNAbs bind similarly or slightly better to cells in an early stage of infection (CD4high). However, despite any such differences between the virion and cell-surface environments, the ability to neutralize virus was significantly correlated with infected-cell binding, and these relationships held whether the inventors considered all infected cells (Gag+) or only late infected cells (Gag+CD4−).

Primary HIV isolates are less sensitive to bNAbs than laboratory-adapted viruses. To investigate factors that may predict the efficacy of bNAb treatment to contribute to HIV cure the inventors felt it important to study the properties of bNAbs against viruses derived from reactivated latent reservoirs. By combining a QVOA approach with isolation of virus from dilutions of CD4+ T cells from different ART-suppressed patients where <50% of wells were p24+, the inventors were able to isolate viruses that were likely clonal to test bNAb binding and neutralization profiles and assess both intra- and inter-patient variability. The inventors observed a considerable level of heterogeneity, even within a given individual, such that in the majority of cases any single bNAb failed to provide universal coverage of an individual's reservoir isolates. However, combinations of two antibodies provided broad coverage both within and across individuals, reaching up to 100% coverage as assessed by binding. Note that as the study population was derived from a single site (Toronto, Canada), from a clinical perspective this assessment of breadth is representative of what might be expected in a single-site study in a North American clade B infected cohort. The inventors propose that the method presented here could be applied to different populations as a means of prioritizing antibody combinations for a given regional population of patients and personalizing individual HIV cure strategies as ART drug resistance is used to guide ART therapy. Clinical use of the QVOA assay will likely be limited by its expense, cell number requirements, and protracted timeline (14 days) for results. However, a notable opportunity is present in the fact that infectious clonal autologous reservoir viruses are generated as a byproduct of the primary measurement. The pairing of quantitative and qualitative assessments of the HIV reservoir in this way has been previously termed the Q2VOA.

The potencies of neutralization observed in the current study are overall weaker than those that have been previously reported using pseudovirus assays—most notably for 2G12, which failed to achieve 80% neutralization for all but two viruses. While this is likely due in part to the use of clinical viral isolates, the inventors also note the role of virus producing cells in modulating sensitivity to neutralization. Studies addressing this issue have reported that T-cell derived virus is more resistant to neutralization than pseudovirus generated by transfected 293T cells and, in particular, that replication competent virus produced by PBMCs are more neutralization resistant than Env matched pseudoviruses. However, there appear to be antibody-specific differences in the level of influence that a producer cell has on sensitivity to neutralization. For example, one study reported that PG9 is not very sensitive to differences in producer cell, while large differences in IC50 have been reported between T cell and pseduovirus for antibody 2G12. These data suggest that producer cells differentially influence the conformations of Env on resulting virions, as well as their densities and glycosylation, or numbers of gp120 molecules in the viral membrane. As PG9 preferentially targets well-ordered, closed, trimeric viral spikes, it indicates that an equal number of well-folded spikes exists on virions produced by either cell type, whereas perhaps bNAbs such as 2G12 can bind equally well to mis-folded trimers and are therefore more sensitive to increases in the latter. Furthermore, the epitopes of certain antibodies, such as 2G12, include glycans, and producer cells can affect glycosylation patterns of gp120. Thus, in addition to the comparison between neutralization and infected-cell binding, the current study contributes a reassessment of bNAb neutralization potency that may be more clinically applicable than data from pseudovirus assays.

In conclusion, the above results provide novel insights into the relationship between infected-cell binding and virus neutralization that may help to guide immunotherapeutic strategies aimed at either curing infection, or enabling durable immune control of viral replication. The degree of intra- and inter-individual variation in bNAb sensitivity within even this geographically discrete clade B population reinforces the importance of utilizing combinations of at least two bNAbs in such therapies. Screening reactivated reservoir viruses for sensitivity to bNAbs, either at an individual or population level, can help select antibody combinations for optimal coverage—for example, with combinations of PG9 and either 3BNC117 or N6 providing potent infected-cell binding coverage of 94% and 72-78% coverage of neutralization (IC80<10 μg/ml) of viruses in the current study population. For the bNAbs that exhibited correlations between infected-cell binding and neutralization, the study indicates that screening for either one of these factors is sufficient to infer that both functions will be brought to bear against reactivated reservoir viruses.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating an individual that carries latent human immunodeficiency virus (HIV) infected cells, the method comprising:
administering to the individual ALT-803, and a broadly neutralizing anti-HIV antibody (bNAb).

2. The method of claim 1, wherein the bNAb is selected from the group consisting of PGT121, 10-1074, 10E8, 10E8v4-V5R-100cF, 2F5, 2G12, 3BNC117, CAP256.VRC26.25, N6, PG9, PGDM1400, VRC01, and VRC07-523.

3. The method of claim 2, further comprising administering a histone deacetylase (HDAC) inhibitor.

4. The method of claim 3, wherein the HDAC inhibitor is vorinostat, panobinostat, valproic acid, phenylbutyrate, entinostat, CI-994, mocetinostat, Viracta 3996, dacinostat, pivanex, givinostat, or belinostat.

5. The method of claim 4, wherein the HDAC inhibitor is administered at least 24 hours before or after the ALT-803.

6. The method of claim 5, wherein a natural killer cell that is genetically modified to express a high affinity CD16 receptor is also administered to the individual.

7. The method of claim 5, wherein a vaccine composition is also administered to the individual, and wherein the vaccine composition is a bacterial vaccine, a yeast vaccine, or a viral vaccine, and further wherein the vaccine composition comprises a recombinant nucleic acid that encodes at least one HIV antigen.

8. The method of claim 7, wherein the bacterial vaccine is an Escherichia coli vaccine that is genetically engineered to have reduced or lacking expression of lipopolysaccharide.

9. The method of claim 7, wherein the yeast vaccine is a Saccharomyces cerevisiae vaccine.

10. The method of claim 7, wherein the viral vaccine is an adenoviral vaccine.

11. The method of claim 6, wherein the natural killer cell is an autologous NK cell, an NK92 cell, an aNK cell, a haNK cell, or a taNK cell.

12. The method of claim 5, further comprising administering a CAR-T cell that has a chimeric antigen receptor (CAR) with an ectodomain that binds to CD2, CD20, or CD32.

13. The method of claim 7, wherein the individual is administered two or more of the vaccine compositions.

14. The method of claim 8, wherein the individual is administered three or more of the vaccine compositions.

15. The method of claim 7, wherein a natural killer cell that is genetically modified to express a high affinity CD16 receptor is also administered to the individual.

* * * * *